US007531174B2

(12) United States Patent
Sanicola-Nadel et al.

(10) Patent No.: US 7,531,174 B2
(45) Date of Patent: May 12, 2009

(54) CRIPTO BLOCKING ANTIBODIES AND USES THEREOF

(75) Inventors: Michele Sanicola-Nadel, Winchester, MA (US); Kevin P. Williams, Chapel Hill, NC (US); Susan Gail Schiffer, Lexington, MA (US); Paul Rayhorn, Foxborough, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 233 days.

(21) Appl. No.: 10/693,538

(22) Filed: Oct. 23, 2003

(65) Prior Publication Data

US 2004/0146940 A1 Jul. 29, 2004

Related U.S. Application Data

(63) Continuation of application No. PCT/US02/11950, filed on Apr. 17, 2002.

(60) Provisional application No. 60/367,002, filed on Mar. 22, 2002, provisional application No. 60/301,091, filed on Jun. 26, 2001, provisional application No. 60/293,020, filed on May 17, 2001, provisional application No. 60/286,782, filed on Apr. 26, 2001.

(51) Int. Cl.
  *A61K 39/395* (2006.01)
  *A61K 38/00* (2006.01)
(52) U.S. Cl. .............. 424/141.1; 424/130.1; 424/178.1; 424/277.1; 530/387.1
(58) Field of Classification Search ............... 435/69.1, 435/320.1, 325, 252.3, 254.11, 69.6; 530/350, 530/300, 399, 387.1; 536/23.5, 23.51, 23.1; 424/141.1, 130.1, 178.1, 277.1
See application file for complete search history.

(56) References Cited

U.S. PATENT DOCUMENTS

| | | | |
|---|---|---|---|
| 5,208,020 A | 5/1993 | Chari et al. | |
| 5,256,643 A | 10/1993 | Persico et al. | |
| 5,264,557 A | 11/1993 | Salomon et al. | |
| 5,530,101 A * | 6/1996 | Queen et al. ............. | 530/387.3 |
| 5,650,285 A | 7/1997 | Salomon et al. | |
| 5,654,140 A | 8/1997 | Persico et al. | |
| 5,792,616 A | 8/1998 | Persico et al. | |
| 5,854,399 A | 12/1998 | Salomon et al. | |
| 5,981,215 A * | 11/1999 | Meissner et al. ........... | 435/69.1 |
| 6,207,153 B1 * | 3/2001 | Dan et al. ................. | 424/138.1 |
| 6,333,410 B1 * | 12/2001 | Chari et al. ................. | 540/456 |
| 6,989,145 B2 | 1/2006 | Shitara et al. | |
| 2003/0232755 A1 * | 12/2003 | Williams et al. ............... | 514/12 |
| 2004/0176576 A1 | 9/2004 | McKenzie et al. | |
| 2005/0255117 A1 * | 11/2005 | Sanicola-Nadel et al. ........................ | 424/155.1 |

FOREIGN PATENT DOCUMENTS

| | | |
|---|---|---|
| JP | 2001-46066 | 2/2001 |
| WO | WO-00/06723 A1 | 2/2000 |
| WO | WO-00/63693 A1 | 10/2000 |
| WO | WO-01/40309 A2 | 6/2001 |
| WO | WO-01/54754 A1 | 9/2001 |
| WO | WO-02/16413 A2 | 2/2002 |
| WO | WO-02/22808 A2 | 3/2002 |
| WO | WO-02/059620 A2 | 8/2002 |
| WO | WO-02/077033 A1 | 10/2002 |
| WO | WO-02/088170 A2 | 11/2002 |
| WO | WO-03/083041 A2 | 10/2003 |

OTHER PUBLICATIONS

William E. Paul, M.D. ed., 3d ed. 1993.*
Qi et al (Journal of cancer. 1994, 69:903-910).*
Adkins, Heather B. et al, "Antibody blockade of the Cripto CFC domain suppresses tumor cell growth in vivo," *the Journal of ClinicalInvestigation*, vol. 112(4):575-587 (2003).
Campbell, Ailsa M., "Monoclonal antibody technology," *Laboratory Techniques in biochemistry and Molecular Biology*, vol. 13, Eds. Burdon, R.H. et al, Elsevier, Amsterdam, New York, Oxford, Champter 1, pp. 1-32 (1984).
Hu, X.F. et al. "Cripto monoclonal antibodies," *Drug News Perspect.*, vol. 18(5):293-303 (2005).
Panico, Luigi et al, "Differential Immunohistochemical Detection of Transforming Growth Factor α, Amphiregulin and Cripto in Human Normal and Malignant Breast Tissue," *Int. J. Cancer*, vol. 65:51-56 (1996).
Schlom, Jeffrey, "Monoclonal Antibodies: They're More and Less Than You Think," *Molecular Foundations of Oncology*, Eds. Broder et al., pp. 95-134 (1991).
International Preliminary Examination Report for Application No. PCT/US02/11950, dated Mar. 9, 2006.
Ciardiello, Fortunato et al., "Antitumor Activity of Combined Blockade of Epiderman Growth Factor Receptor and Protein Kinase A," *Journal of the National Cancer Institute*, vol. 88(23):1770-1776 (1996).
Dono, Rosanna et al., "Isolation and Characterization of the CRIPTO Autosomal Gene and Its X-linked Related Sequence," *Am. J. Hum. Genet.*, vol. 49:555-565 (1991).
Friess, Helmut et al., "CRIPTO, A Member of the Epidermal Growth Factor Family, is Over-expressed in Human Pancreatic Cancer and Chronic Pancratitis," *Int. J. Cancer*, vol. 56:668-674 (1994).

(Continued)

*Primary Examiner*—Sheela J Huff
(74) *Attorney, Agent, or Firm*—Lahive & Cockfield, LLP; Megan E. Williams

(57) ABSTRACT

The invention provides Cripto blocking antibodies, or biologically functional fragments thereof, and uses thereof. Antibodies which bind Cripto and modulate Cripto signaling are provided. Antibodies which bind Cripto and block the interaction between Cripto and ALK4 are provided. Antibodies which bind Cripto and modulate tumor growth are also provided. Antibodies which bind Cripto, modulate signaling, and modulate tumor growth are also provided. Antibodies which bind Cripto, block the interaction between Cripto and ALK4 and modulate tumor growth are provided. The invention also provides methods of using these antibodies in therapeutic, diagnostic, and research applications.

228 Claims, 3 Drawing Sheets

OTHER PUBLICATIONS

Sugino, Yukio, Ed. "Biotechnology Series, Monoclonal Antibody," 1st Edition, Kodansha Ltd., Tokyo, Japan, p. 1-16 (1986).

Japanese Office Action for Application No. 2002-585468, dated Nov. 2, 2007.

Bianco, Caterina, et al., "Cripto-1 Indirectly Stimulates the Tyrosine Phosphorylation of *erb* B-4 through a Novel Receptor," *The Journal of Biological Chemistry*, vol. 274(13):8624-8629 (1999).

Brandt, Ralf, et al., "Identification and Biological Characterization of an Epidermal Growth Factor-related Protein: Cripto-1," *The Journal of Biological Chemistry*, vol. 269(25):17320-17328 (1994).

Ciardiello, Fortunato, et al., "Inhibition of CRIPTO expression and tumorigenicity in human colon cancer cells by antisense RNA and oligodeoxynucleotides," *Oncogene*, vol. 9:291-298 (1994).

Ciccodicola, Alfredo, et al., "Molecular characterization of a gene of the 'EGF family' expressed in undifferentiated human NTERA2 teratocarcinoma cells," *The EMBO Journal*, vol. 8(7):1987-1991 (1989).

Dublin, Edwin A., et al., "Amphiregulin and cripto overexpression in breast cancer: relationship with prognosis and clinical and molecular variables," *International Journal of Oncology*, vol. 7:617-622 (1995).

Ebert, Andreas D., et al., "Cripto-1 Induces Phosphatidylinositol 3'-Kinase-dependent Phosphorylation of AKT and Glycogen Synthase 3β in Human Cervical Carcinoma Cells," *Cancer Research*, vol. 59:4502-4505 (1999).

Kannan, Subha, et al., "Cripto Enhances the Tyrosine Phosphorylation and Shc and Activates Mitogen-activated Protein Kinase (MAPK) in Mammary Epithelial Cells," *The Journal of Biological Chemistry*, vol. 272(6):3330-3335 (1997).

Normanno, Nicola, et al., "Expression of amphiregulin, cripto-1, and heregulin α in human breast cancer cells," *International Journal of Oncology*, vol. 2:903-911 (1993).

Saeki, Toshiaki, et al., "Expression of cripto-1 in human colorectal adenomas and carcinomas is related to the degree of dysplasia," *International Journal of Oncology*, vol. 5:445-451 (1994).

Saeki, Toshiaki, et al., "Immunohistochemical detection of cripto-1, amphiregulin and transforming growth factor alpha in human gastric carcinomas and intestinal metaplasias," *International Journal of Oncology*, vol. 5:215-223 (1994).

Salomon, D.S., et al., "The EGF-CFC family: novel epidermal growth factor-related proteins in development and cancer," *Endocrine-Related Cancer*, vol. 7:199-226 (2000).

International Search Report Application No. PCT/US02/11950, dated Sep. 5, 2003.

* cited by examiner

SEQUENCE LISTING

```
<160> NUMBER OF SEQ ID NOS: 2

<210> SEQ ID NO 1
<211> LENGTH: 188
<212> TYPE: PRT
<213> ORGANISM: Homo Sapiens

<400> SEQUENCE: 1

Met Asp Cys Arg Lys Met Ala Arg Phe Ser Tyr Ser Val Ile Trp Ile
 1               5                  10                  15

Met Ala Ile Ser Lys Val Phe Glu Leu Gly Leu Val Ala Gly Leu Gly
                20                  25                  30

His Gln Glu Phe Ala Arg Pro Ser Arg Gly Tyr Leu Ala Phe Arg Asp
            35                  40                  45

Asp Ser Ile Trp Pro Gln Glu Glu Pro Ala Ile Arg Pro Arg Ser Ser
        50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
            180                 185

<210> SEQ ID NO 2
<211> LENGTH: 188
<212> TYPE: PRT
<213> ORGANISM: Homo Sapiens

<400> SEQUENCE: 2

Met Asp Cys Arg Lys Met Val Arg Phe Ser Tyr Ser Val Ile Trp Ile
 1               5                  10                  15

Met Ala Ile Ser Lys Ala Phe Glu Leu Gly Leu Val Ala Gly Leu Gly
                20                  25                  30
```

-continued

```
His Gln Glu Phe Ala Arg Pro Ser Arg Gly Asp Leu Ala Phe Arg Asp
     35                  40                  45
Asp Ser Ile Trp Pro Gln Glu Glu Pro Ala Ile Arg Pro Arg Ser Ser
     50                  55                  60
Gln Arg Val Leu Pro Met Gly Ile Gln His Ser Lys Glu Leu Asn Arg
65                       70                  75                  80
Thr Cys Cys Leu Asn Gly Gly Thr Cys Met Leu Glu Ser Phe Cys Ala
             85                  90                  95
Cys Pro Pro Ser Phe Tyr Gly Arg Asn Cys Glu His Asp Val Arg Lys
                 100                 105                 110
Glu Asn Cys Gly Ser Val Pro His Asp Thr Trp Leu Pro Lys Lys Cys
         115                 120                 125
Ser Leu Cys Lys Cys Trp His Gly Gln Leu Arg Cys Phe Pro Gln Ala
     130                 135                 140
Phe Leu Pro Gly Cys Asp Gly Leu Val Met Asp Glu His Leu Val Ala
145                 150                 155                 160
Ser Arg Thr Pro Glu Leu Pro Pro Ser Ala Arg Thr Thr Thr Phe Met
             165                 170                 175
Leu Ala Gly Ile Cys Leu Ser Ile Gln Ser Tyr Tyr
             180                 185
```

US 7,531,174 B2

CRIPTO BLOCKING ANTIBODIES AND USES THEREOF

RELATED APPLICATIONS

This is a continuation of PCT/US02/11950, filed Apr. 17, 2002, which claims the benefit of U.S. Ser. No. 60/367,002, filed Mar. 22, 2002, and U.S. Ser. No. 60/301,091, filed Jun. 26, 2001, and U.S. Ser. No. 60/293,020, filed on May 17, 2001, and U.S. Ser. No. 60/286,782, filed on Apr. 26, 2001. The entire disclosure of each of the aforesaid patent applications are incorporated herein by reference.

TECHNICAL FIELD OF THE INVENTION

The present invention relates generally to the fields of genetics and cellular and molecular biology. More particularly, the invention relates to antibodies which bind to and modulate the signaling of Cripto, kits comprising such antibodies, and methods which use the antibodies.

BACKGROUND OF THE INVENTION

Cripto is a cell surface protein of 188 amino acid residues serendipitously isolated in a cDNA screen of a human embryonic carcinoma library (Ciccodicola et al., 1989, EMBO J., vol. 8, no. 7, pp. 1987-1991). The Cripto protein has at least two notable domains: a cysteine-rich domain, and a domain first characterized as similar to the domain found in the epidermal growth factor (EGF) family. Cripto was originally classified as a member of the EGF family (Ciccodicola et al., supra); however, subsequent analysis showed that Cripto did not bind any of the known EGF receptors and its EGF-like domain was actually divergent from the EGF family (Bianco et al., 1999, J. Biol. Chem., 274:8624-8629).

The Cripto signaling pathway has remained elusive despite continued investigation, with the literature supporting activation of several different pathways, including a MAP kinase pathway (DeSantis et al., 1997, Cell Growth Differ., 8:1257-1266; Kannan et al., 1997, J. Biol. Chem., 272:3330-3335), the TGF-β pathway (Gritsman et al., 1999, Development, 127:921-932; Schier et al., 2000, Nature, 403:385-389), possible interactions with the Wnt pathway (Salomon et al., Endocr Relat Cancer. 2000 December;7(4):199-226; and cross talk with the EGF pathway (Bianco et al., 1999, J. Biol. Chem., 274:8624-8629).

U.S. Pat. No. 5,256,643 and two divisional applications related thereto (U.S. Pat. Nos. 5,654,140 and 5,792,616), disclose a human Cripto gene, Cripto protein, and antibodies to Cripto.

U.S. Pat. No. 5,264,557 and three divisional applications related thereto (U.S. Pat. Nos. 5,620,866, 5,650,285, and 5,854,399), disclose a human Cripto-related gene and protein. Also disclosed are antibodies which bind to the Cripto-related protein but do not cross react by binding to the Cripto protein itself.

Cripto protein overexpression is associated with many tumor types (including but not limited to breast, testicular, colon, lung, ovary, bladder, uterine, cervical, pancreatic, and stomach), as demonstrated by immunostaining of human tissue with rabbit polyclonal antibodies raised against small cripto peptides. Panico et al., 1996, Int. J. Cancer, 65: 51-56; Byrne et al., 1998, J Pathology, 185:108-111; De Angelis et al., 1999, Int J Oncology, 14:437-440. The art is therefore in need of means of controlling, restricting, and/or preventing such overexpression, modulating Cripto signaling, and modulating the consequences of Cripto expression (i.e., promotion and/or maintenance of cell transformation).

SUMMARY OF THE INVENTION

Figure 1:
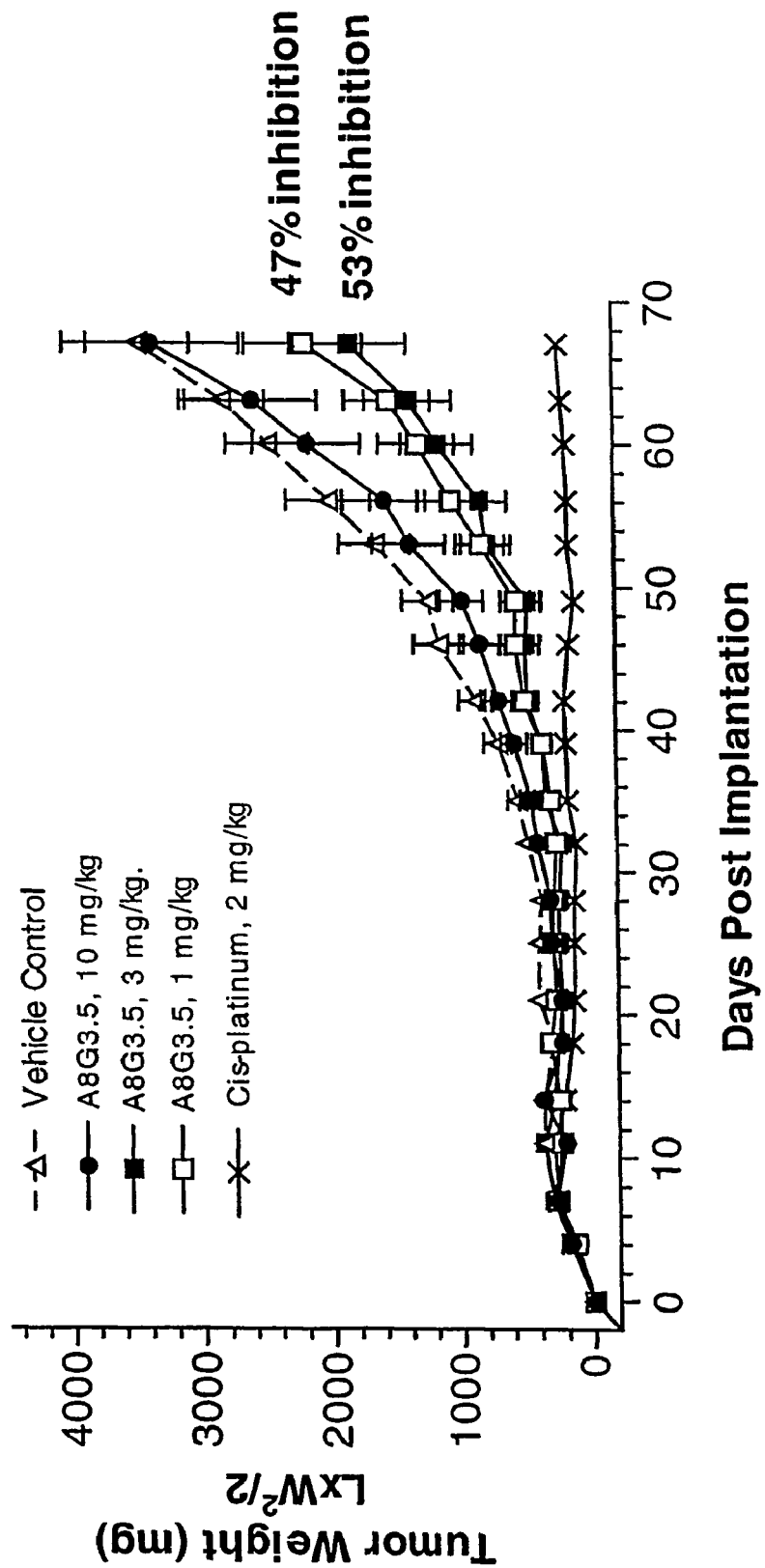
FIG. 1 shows the response of the NCCIT, human testicular carcinoma cell line, to anti-CFC blocking Cripto mAb A8G3.5.

The present invention provides novel antibodies which specifically bind to Cripto, and methods of making and using such antibodies. The invention also provides antibodies which bind to Cripto, and modulate Cripto signaling or protein interaction, e.g., an antibody which binds to Cripto such that the signal resulting from a protein interaction with Cripto is modulated downward. The invention also provides antibodies which bind to Cripto and block the interaction between Cripto and ALK4. The invention also provides antibodies which bind to Cripto and modulate tumor growth. The invention also provides antibodies which bind to Cripto, modulate Cripto signaling and modulate tumor growth. The invention also provides antibodies which bind to Cripto, block the interaction between Cripto and ALK4 and modulate tumor growth In one aspect of the invention, the antibody of the present invention specifically binds to an epitope selected from the group of epitopes to which antibodies A6C12.11, A6F8.6 (ATCC ACCESSION NO. PTA-3318), A7H1.19, A8F1.30, A8G3.5 (ATCC ACCESSION NO. PTA-3317), A8H3.1 (ATCC ACCESSION NO. PTA-3315), A8H3.2, A19A10.30, A10B2.18 (ATCC ACCESSION NO. PTA-3311), A27F6.1 (ATCC ACCESSION NO. PTA-3310), A40G12.8 (ATCC ACCESSION NO. PTA-3316), A2D3.23, A7A10.29, A9G9.9, A15C12.10, A15E4.14, A17A2.16, A17G12.1 (ATCC ACCESSION NO. PTA-3314), A17H6.1, A18B3.11 (ATCC ACCESSION NO. PTA-3312), A19E2.7, B3F6.17 (ATCC ACCESSION NO. PTA-3319), B6G7.10 (ATCC ACCESSION NO. PTA-3313), B11H8.4 bind.

In another aspect of the invention, the antibody of the present invention specifically binds to an epitope in the ligand/receptor binding domain of Cripto. Cripto can be selected from CR-1 (SEQ ID NO:1) or CR-3 (SEQ ID NO:2). In a more particular embodiment, antibodies that specifically binds to the epitope in the ligand/receptor binding domain include for example A6C12.11, A6F8.6 (ATCC ACCESSION NO. PTA-3318), A8G3.5 (ATCC ACCESSION NO. PTA-3317), A19A10.30, A8H3.1 (ATCC ACCESSION NO. PTA-3315), A27F6.1 (ATCC ACCESSION NO. PTA-3310), A40G12.8 (ATCC ACCESSION NO. PTA-3316), A17G12.1 (ATCC ACCESSION NO. PTA-3314), A18B3.11 (ATCC ACCESSION NO. PTA-3312) and B6G7.10 (ATCC ACCESSION NO. PTA-3313).

In one embodiment the epitope to which the antibodies of the present invention bind is in an EGF-like domain. Antibodies that specifically bind to the epitope in the EGF-like domain include but are not limited to A40G12.8 (ATCC ACCESSION NO. PTA-3316), A8H3.1 (ATCC ACCESSION NO. PTA-3315), A27F6.1 (ATCC ACCESSION NO. PTA-3310), B6G7.10 (ATCC ACCESSION NO. PTA-3313), A17G12.1 (ATCC ACCESSION NO. PTA-3314) and A18B3.11 (ATCC ACCESSION NO. PTA-3312).

In another embodiment the epitope to which the antibodies of the present invention bind is in a cys-rich domain. Antibodies that specifically bind to the epitope in the cys-rich domain include but are not limited to A19A10.30, A8G3.5 (ATCC ACCESSION NO. PTA-3317), A6F8.6 (ATCC ACCESSION NO. PTA-3318) and A6C12.11.

In another embodiment the epitope to which the antibodies of the present invention bind is in the domain spanning amino acid residues 46-62 of Cripto. Antibodies that specifically bind to the epitope in the domain spanning amino acid residues 46-62 of Cripto include but are not limited to A10B2.18 (ATCC ACCESSION NO. PTA-3311), B3F6.17 (ATCC ACCESSION NO. PTA-3319) and Al7A2.16.

The present inventions also comtemplate antibodies which binds specifically to Cripto and are capable of modulating Cripto signaling. Antibodies that bind specifically to Cripto and are capable of modulating Cripto signaling, include but are not limited to, A40G12.8 (ATCC ACCESSION NO. PTA-3316), A8H3.1 (ATCC ACCESSION NO. PTA-3315), A27F6.1 (ATCC ACCESSION NO. PTA-3310), and A6C12.11. In one embodiment the antibodies of the present invention which binds specifically to Cripto and are capable of modulating Cripto signaling bind to an epitope in an EGF-like domain or a cys-rich domain of Cripto.

The present inventions also comtemplate antibodies which binds specifically to Cripto and blocks the interaction between Cripto and ALK4. Antibodies that bind specifically to Cripto and are capable of blocking the interaction between Cripto and ALK4, include but are not limited to, A8G3.5 (ATCC ACCESSION NO. PTA-3317), A6F8.6 (ATCC ACCESSION NO. PTA-3318) and A6C12.11. In one embodiment the antibodies of the present invention which binds specifically to Cripto and are capable of blocking the interaction between Cripto and ALK4 bind to an epitope in an EGF-like domain or a cys-rich domain of Cripto.

In another aspect, the present invention comtemplates antibodies which bind specifically to Cripto and are capable of modulating tumor growth. Antibodies that specifically bind to Cripto and are capable of modulating tumor growth include but are not limited to, A27F6.1 (ATCC ACCESSION NO. PTA-3310), B6G7.10 (ATCC ACCESSION NO. PTA-3313) and A8G3.5 (ATCC ACCESSION NO. PTA-3317).

In one embodiment the antibodies of the present invention which bind specifically to Cripto and are capable of modulating tumor growth bind to an epitope in an EGF-like domain or a cys-rich domain of Cripto.

In yet another aspect, the present invention comtemplates antibodies which bind specifically to Cripto, which are capable of modulating Cripto signaling, and which are capable of modulating tumor growth. Antibodies that specifically bind to Cripto, which are capable of modulating Cripto signaling, and which are capable of modulating tumor growth, include but are not limited to A27F6.1 (ATCC ACCESSION NO. PTA-3310).

In one embodiment the antibodies of the present invention which bind specifically to Cripto, which are capable of modulating Cripto signaling, and which are capable of modulating tumor growth bind to an epitope in an EGF-like domain or a cys-rich domain of Cripto.

In yet another aspect, the present invention comtemplates antibodies which bind specifically to Cripto, which are capable of blocking the interaction between Cripto and ALK4, and which are capable of modulating tumor growth. Antibodies that specifically bind to Cripto, which are capable of blocking the interaction between Cripto and ALK4, and which are capable of modulating tumor growth, include but are not limited to A8G3.5 (ATCC ACCESSION NO. PTA-3317).

The hybridoma cells A27F6.1, A10B2.18, A18B3.11, B6G7.10, A17G12.1. A8H3.1, A40G12.8, A8G3.5, A6F8.6 and B3F6.17 were deposited with the American Type Culture Collection at 12301 Parklawn Drive, Rockville, Md. 20852 under the terms of the Budapest Treaty on Jan. 19, 2001 as ATCC Accession No. PTA-3310 (A27F6.1), ATCC Accession No. PTA-3311 (A10B2.18), ATCC Accession No. PTA-3312 (A18B3.11), ATCC Accession No. PTA-3313 (B6G7.10), ATCC Accession No. PTA-3314 (A17G12.1), ATCC Accession No. PTA-3315 (A8H3.1), ATCC Accession No. PTA-3316 (A40G12.8), ATCC Accession No. PTA-3317 (A8G3.5), ATCC Accession No. PTA-3318 (A6F8.6) and ATCC Accession No. PTA-3319 (B3F6.17).

The antibodies of the present invention include but are not limited to monoclonal, polyclonal, humanized, chimeric and human antibodies.

The present invention also provides for a composition for administration to a subject having a tumor that expresses Cripto comprising at least one of the antibodies described above. In a more particular embodiment the subject is human. The composition may include a pharmaceutically acceptable excipient. The antibodies described above can be conjugated to a chemotherapeutic agent or be provided in combination with a nonconjugated chemotherapeutic.

Contemplated in another aspect of the invention are methods of modulating growth of tumor cells in vitro in a sample comprising the step of adding to the sample the compositions described above.

Also comtemplated are methods of modulating growth of tumor cells in vivo in a subject comprising the step of administering to the subject an effective amount of the compositions described above. In a particular embodiment the subject is human.

Another aspect of the invention are methods of treating subjects having a tumor that over-expresses Cripto comprising administering to the subject the compositions described above in an effective amount. Compositions for administration may include pharmaceutically acceptable excipients, antibodies conjugated to chemotherapeutic agents and antibodies administered in combination with nonconjugated chemotherapeutic agents The methods of the present invention are particularly useful in modulating growth of tumor cells and/or treating a subject (i.e. a human) having a tumor where the tumor cell is selected from breast, testicular, colon, lung, ovary, bladder, uterine, cervical, pancreatic, and stomach tumor cells.

In yet another embodiment, the present invention contemplates methods of determining whether a tissue expresses Cripto, comprising the step of analyzing tissue from the subject in an immunoassay using any of the antibodies described above. Also contemplated are methods of determining whether a cell line overexpresses Cripto, comprising the step of analyzing the cell line in an immunoassay using any of the antibodies described above.

These and other aspects of the invention are set forth in greater detail below in the Detailed Description of the Invention.

DETAILED DESCRIPTION OF THE INVENTION

Antibodies that specifically bind to Cripto and their uses for modulating Cripto signaling or protein interaction, and/or block the interaction between Cripto and ALK4, and/or modulate the growth of tumor cells have been discovered.

Various classes of antibodies that specifically bind to Cripto have been discovered, including, for example, antibodies that specifically bind to an epitope in the ligand/receptor binding domain of either a native Cripto protein or a denatured form of Cripto; antibodies that bind an EGF-like domain, a cys-rich domain, or a peptide (e.g., from about 3 to about 20 amino acids) from the region comprising amino acid residues 46 to 150; antibodies that bind Cripto and modulate Cripto signalling; antibodies that bind Cripto and modulate tumor cell growth; and antibodies that bind to Cripto, modulate Cripto signaling, and modulate tumor cell growth. These antibodies are selected using conventional in vitro assays for selecting antibodies which bind the ligand/receptor binding domain, modulate Cripto signaling, or modulate tumor cell growth.

The methods of this invention are useful in the therapy of malignant or benign tumors of mammals where the growth rate of the tumor (which is an abnormal rate for the normal tissue) is at least partially dependent upon Cripto. Abnormal growth rate is a rate of growth which is in excess of that required for normal homeostasis and is in excess of that for normal tissues of the same origin.

Definitions

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art.

As used herein, the term "region" means a physically contiguous portion of the primary structure of a biomolecule. In the case of proteins, a region is defined by a contiguous portion of the amino acid sequence of that protein.

As used herein, the term "domain" refers to a structural part of a biomolecule that contributes to a known or suspected function of the biomolecule. Domains may be co-extensive with regions or portions thereof; domains may also incorporate a portion of a biomolecule that is distinct from a particular region, in addition to all or part of that region. Examples of protein domains include, but are not limited to the extracellular domain (spans from about residue 31 to about residue 188 of Cripto, including Cripto, CR-1 (SEQ ID NO: 1) and CR-3 (SEQ ID NO:2)) and transmembrane domain (spans from about residue 169 to about residue 188 of Cripto, including Cripto, CR-1 (SEQ ID NO: 1) and CR-3 (SEQ ID NO:2)). A ligand/receptor binding domain of the Cripto protein spans from about residue 75 to about residue 150 of Cripto, including Cripto, CR-1 (SEQ ID NO: 1) and CR-3 (SEQ ID NO:2) and includes the EGF-like domain of Cripto, which spans, for example, from about residue 75 to about residue 112 of Cripto, including Cripto, CR-1 (SEQ ID NO: 1) and CR-3 (SEQ ID NO:2) and the cysteine-rich domain of Cripto, which spans, for example, from about residue 114 to about residue 150 of Cripto, including Cripto, CR-1 (SEQ ID NO: 1) and CR-3 (SEQ ID NO:2). For example, many monoclonal antibodies of the present invention have been identified as binding to the EGF-like or cys-rich domains. Additionally monoclonal antibody A10B2.18 (ATCC ACCESSION NO. PTA-3311), B3F6.17 (ATCC ACCESSION NO. PTA-3319) and A17A2.16 have been identified as binding to an epitope formed in a domain in the region spanning amino acid residues 46-62, upstream of the EGF-like domain. See Example 3 below. An epitope in the ligand/receptor binding domain is an epitope, whether formed in the conformational native Cripto protein, or the denatured Cripto protein, to which antibodies may bind.

As used herein, the term "antibody" is meant to refer to complete, intact antibodies, and Fab, Fab', F(ab)2, and other fragments thereof. Complete, intact antibodies include, but are not limited to, monoclonal antibodies such as murine monoclonal antibodies, polyclonal antibodies, chimeric antibodies, human antibodies, and humanized antibodies. Various forms of antibodies may be produced using standard recombinant DNA techniques (Winter and Milstein, Nature 349: 293-99, 1991). For example, "chimeric" antibodies may be constructed, in which the antigen binding domain from an animal antibody is linked to a human constant domain (an antibody derived initially from a nonhuman mammal in which recombinant DNA technology has been used to replace all or part of the hinge and constant regions of the heavy chain and/or the constant region of the light chain, with corresponding regions from a human immunoglobulin light chain or heavy chain) (see, e.g., Cabilly et al., U.S. Pat. No. 4,816,567; Morrison et al., Proc. Natl. Acad. Sci. 81: 6851-55, 1984). Chimeric antibodies reduce the immunogenic responses elicited by animal antibodies when used in human clinical treatments.

In addition, recombinant "humanized" antibodies may be synthesized. Humanized antibodies are antibodies initially derived from a nonhuman mammal in which recombinant DNA technology has been used to substitute some or all of the amino acids not required for antigen binding with amino acids from corresponding regions of a human immunoglobulin light or heavy chain. That is, they are chimeras comprising mostly human immunoglobulin sequences into which the regions responsible for specific antigen-binding have been inserted (see, e.g., PCT patent application WO 94/04679). Animals are immunized with the desired antigen, the corresponding antibodies are isolated and the portion of the variable region sequences responsible for specific antigen binding are removed. The animal-derived antigen binding regions are then cloned into the appropriate position of the human antibody genes in which the antigen binding regions have been deleted. Humanized antibodies minimize the use of heterologous (inter-species) sequences in antibodies for use in human therapies, and are less likely to elicit unwanted immune responses. Primatized antibodies can be produced similarly.

Another embodiment of the invention includes the use of human antibodies, which can be produced in nonhuman animals, such as transgenic animals harboring one or more human immunoglobulin transgenes. Such animals may be used as a source for splenocytes for producing hybridomas, as is described in U.S. Pat. No. 5,569,825.

Antibody fragments and univalent antibodies may also be used in the methods and compositions of this invention. Univalent antibodies comprise a heavy chain/light chain dimer bound to the Fc (or stem) region of a second heavy chain. "Fab region" refers to those portions of the chains which are roughly equivalent, or analogous, to the sequences which comprise the Y branch portions of the heavy chain and to the light chain in its entirety, and which collectively (in aggregates) have been shown to exhibit antibody activity. A Fab protein includes aggregates of one heavy and one light chain (commonly known as Fab'), as well as tetramers which correspond to the two branch segments of the antibody Y, (commonly known as F(ab)2), whether any of the above are covalently or non-covalently aggregated, so long as the aggregation is capable of specifically reacting with a particular antigen or antigen family.

Any of the antibodies of the invention may optionally be conjugated to a chemotherapeutic, as defined below.

As used herein, the term "binding" means the physical or chemical interaction between two proteins or compounds or associated proteins or compounds or combinations thereof, including the interaction between an antibody and a protein.

Binding includes ionic, non-ionic, hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates. Binding may be detected in many different manners. Methods of detecting binding are well-known to those of skill in the art.

As used herein, "an antibody capable of internalizing Cripto" means an antibody which enters the cell while removing Cripto from the cell surface. One can screen for Cripto antibodies which are capable of internalizing Cripto by using fluorescent labeled Cripto monoclonal antibodies. In order to determine which antibodies internalize into the Cripto positive cells one can assay for the uptake of the fluorescent signal of the antibodies into the cells by viewing the cells under a fluorescent and/or confocal microscope. Those antibodies that get internalized will be seen as fluorescent signals in the cytoplasmic and or cellular vesicles. Non-limiting examples of Cripto antibodies capable of internalizing Cripto include A27F6.1 and B3F6.17.

As used herein, the term "compound" means any identifiable chemical or molecule, including, but not limited to, ion, atom, small molecule, peptide, protein, sugar, nucleotide, or nucleic acid, and such compound can be natural or synthetic.

As used herein, the terms "modulates" or "modifies" means an increase or decrease in the amount, quality, or effect of a particular activity or protein.

As used herein, the term "modulate Cripto signaling" means an increase or decrease in the amount, quality, or effect of Cripto activity, by about 5%, preferably 10%, more preferably 20%, more preferably 30%, more preferably 40%, more preferably 50%, more preferably 60%, more preferably 70%, more preferably 80%, more preferably 90%, and most preferably 100%,. Activity may be measured by assays known in the art, such as the null cell assay shown in Example 3. In another embodiment, protein interaction between Cripto and another protein is similarly modulated downward via binding of the antibodies of the invention.

As used herein, the term "blocking the interaction between Cripto and ALK 4" means an increase or decrease in the interaction, i.e. binding, between Cripto and ALK4, by about 5%, preferably 10%, more preferably 20%, more preferably 30%, more preferably 40%, more preferably 50%, more preferably 60%, more preferably 70%, more preferably 80%, more preferably 90%, and most preferably 100%,. Activity may be measured by assays known in the art, such as the binding assay shown in Example 8.

As used herein, the term "modulate growth of tumor cells in vitro" means an increase or decrease in the number of tumor cells, in vitro, by about 5%, preferably 10%, more preferably 20%, more preferably 30%, more preferably 40%, more preferably 50%, more preferably 60%, more preferably 70%, more preferably 80%, more preferably 90%, and most preferably 100%. In vitro modulation of tumor cell growth may be measured by assays known in the art, such as the GEO cell soft agar assay shown in Example 4.

As used herein, the term "modulate growth of tumor cells in vivo" means an increase or decrease in the number of tumor cells, in vivo, by about 5%, preferably 10%, more preferably 20%, more preferably 30%, more preferably 40%, more preferably 50%, more preferably 60%, more preferably 70%, more preferably 80%, more preferably 90%, and most preferably 100%. In vivo modulation of tumor cell growth may be measured by assays known in the art, such as the one shown in Example 5.

The term "preventing" refers to decreasing the probability that an organism contracts or develops an abnormal condition.

The term "treating" refers to having a therapeutic effect and at least partially alleviating or abrogating an abnormal condition in the organism. Treating includes maintenance of inhibited tumor growth, and induction of remission.

The term "therapeutic effect" refers to the inhibition of an abnormal condition. A therapeutic effect relieves to some extent one or more of the symptoms of the abnormal condition. In reference to the treatment of abnormal conditions, a therapeutic effect can refer to one or more of the following: (a) an increase or decrease in the proliferation, growth, and/or differentiation of cells; (b) inhibition (i.e., slowing or stopping) or promotion of cell death; (c) inhibition of degeneration; (d) relieving to some extent one or more of the symptoms associated with the abnormal condition; and (e) enhancing the function of a population of cells. Compounds demonstrating efficacy against abnormal conditions can be identified as described herein.

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes, or in another organism. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques and carrier techniques. Administration may be accomplished by the many modes known in the art, e.g., oral, intravenous, intraperitoneal, intramuscular, and the like. When used in in vivo therapy, the antibodies of the subject invention are administered to a patient in effective amounts. As used herein an "effective amount" is an amount sufficient to effect beneficial or desired clinical results (i.e., amounts that eliminate or reduce the patient's tumor burden). An effective amount can be administered in one or more administrations. For purposes of this invention, an effective amount of the antibodies of the present invention is an amount of the antibodies that is sufficient to ameliorate, stabilize, or delay the development of the Cripto-associated disease state, particularly Cripto-associated tumors. Detection and measurement of these indicators of efficacy are discussed below. An example of a typical treatment regime includes administering by intravenous infusion to the subject antibodies of the invention on a weekly schedule, at a dose of about 2-5 mg/kg. The antibodies are administered in an outpatient chemoinfusion unit, unless the patient requires hospitalization. Other administration regimes known in the art are also contemplated.

The abnormal condition can also be prevented or treated by administering an antibody of the invention to a group of cells having an aberration in a signal transduction pathway to an organism. The effect of administering a compound on organism function can then be monitored. The organism is preferably a human.

"Cripto overexpression" is intended to mean the expression of Cripto by a tissue which expression is greater than the Cripto expression of adjacent normal tissue in a statistically significant amount.

"Chemotherapeutics" refers to any agents identified in the art as having therapeutic effect on the inhibition of tumor growth, maintenace of inhibited tumor growth, and/or induction of remission, such as natural compounds, synthetic compounds, proteins, modified proteins, and radioactive compounds. Chemotherapeutic agents contemplated herewith include agents that can be conjugated to the antibodies of the present invention or alternatively agents that can be used in combination with the antibodies of the present invention without being conjugated to the antibody. Exemplary chemotherapeutics that can be conjugated to the antibodies of the present invention include, but are not limited to radioconjugates (90Y, 131I, 99mTc, 111In, 186Rh, et al.), tumor-activated prodrugs (maytansinoids, CC-1065 analogs, clicheamicin derivatives, anthracyclines, vinca alkaloids, et al.), ricin, diptheria toxin, pseudomonas exotoxin.

Chemotherapeutic agents may be used in combination with the antibodies of the invention, rather than being conjugated thereto (i.e. nonconjugated chemotherapeutics), include, but are not limited to the following: platinums (i.e. cis platinum), anthracyclines, nucleoside analogs (purine and pyrimidine), taxanes, camptothecins, epipodophyllotoxins, DNA alkylating agents, folate antagonists, vinca alkaloids, ribonucleotide reductase inhibitors, estrogen inhibitors, progesterone inhibitors, androgen inhibitors, aromatase inhibitors, interferons, interleukins, monoclonal antibodies, taxol, camptosar, adriamycin (dox), 5-FU and gemcitabine. Such chemotherapeutics may be employed in the practice of the invention in combination with the antibodies of the invention by coadministration of the antibody and the nonconjugated chemotherapeutic.

"Pharmaceutically acceptable carrier or excipient" refers to biologically inert compounds known in the art and employed in the administration of the antibodies of the invention. Acceptable carriers are well known in the art and are described, for example, in *Remington's Pharmaceutical Sciences*, Gennaro, ed., Mack Publishing Co., 1990. Acceptable carriers can include biocompatible, inert or bioabsorbable salts, buffering agents, oligo- or polysaccharides, polymers, viscoelastic compound such as hyaluronic acid, viscosity-improving agents, preservatives, and the like.

A "subject" refers to vertebrates, particularly members of a mammalian species, and includes but is not limited to domestic animals, sports animals, and primates, including humans.

ANTIBODIES OF THE INVENTION

The antibodies of the invention specifically bind to Cripto: As used herein, Cripto includes the CR-1 Cripto protein, the CR-3 Cripto protein, and fragments thereof. Such fragments may be entire domains, such as the extracellular or intracellular domains, the EGF-like domain, the cys-rich domain, the receptor binding domain, and the like. Such fragments may also include contiguous and noncontiguous epitopes in any domain of the Cripto protein.

In a one embodiment, the antibodies of the invention bind to an epitope in the EGF-like domain of Cripto. The EGF-like domain spans from about amino acid residue 75 to about amino acid residue 112 of the mature Cripto protein. Epitopes in the EGF-like domain may comprise linear or nonlinear spans of amino acid residues. Example of linear epitopes contemplated include but are not limited to about residues 75-85, 80-90, 85-95, 90-100, 95-105, 100-110, or 105-112. In one embodiment, the epitope in the EGF domain is an epitope formed in the conformational native Cripto protein versus a denatured Cripto protein.

In another embodiment, the antibodies of the invention bind to an epitope in the cys-rich domain of Cripto. The cys-rich domain spans from about amino acid residue 114 to about amino acid residue 150 of the mature Cripto protein. Epitopes in the cys-rich domain may comprise linear or nonlinear spans of amino acid residues. Example of linear epitopes contemplated include but are not limited to about residues 114-125, 120-130, 125-135, 130-140, 135-145, or 140-150. In one embodiment, the epitope in the cys-rich domain is an epitope formed in the conformational native Cripto protein versus a denatured Cripto protein Once antibodies are generated, binding of the antibodies to Cripto may be assayed using standard techniques known in the art, such as ELISA, while the presence of Cripto on a cell surface may be assayed using flow cytometry (FACS), as shown in Example 2. Any other techniques of measuring such binding may alternatively be used.

The present invention provides antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for Cripto or fragments thereof. Antibody fragments, including Fab, Fab', F(ab')$_2$, and F$_v$, are also provided by the invention. The terms "specific" and "selective," when used to describe binding of the antibodies of the invention, indicates that the variable regions of the antibodies of the invention recognize and bind Cripto polypeptides. It will be understood that specific antibodies of the invention may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention The 188 amino acid sequence for CR-1 is as follows:

MDCRKMARFSYSVIWIMAISKVFELGLVAGLGHQEFARPSRGYLAFRDDS  [SEQ ID NO: 1]

IWPQEEPAIRPRSSQRVPPMGIQHSKELNRTCCLNGGTCMLGSFCACPPS

FYGRNCEHDVRKENCGSVPHDTWLPKKCSLCKCWHGQLRCFPQAFLPGCD

GLVMDEHLVASRTPELPPSARTTTFMLVGICLSIQSYY

The 188 amino acid sequence for CR-3 is as follows:

MDCRKMVRFSYSVIWIMAISKAFELGLVAGLGHQEFARPSRGDLAFRDDS  [SEQ ID NO: 2]

IWPQEEPAIRPRSSQRVLPMGIQHSKELNRTCCLNGGTCMLESFCACPPSF

YGRNCEHDVRKENCGSVPHDTWLPKKCSLCKCWHGQLRCFPQAFLPGCDGL

VMDEHLVASRTPELPPSARTTTFMLAGICLISIQSYY (i.e. antibodies that specifically bind to an epitope the ligand/receptor binding domain and the domain spanning amino acid residues 46-62) are well known and routinely practiced in the art. For a comprehensive discussion of such assays, see Harlow et al. (Eds.), *Antibodies A Laboratory Manual*; Cold Spring Harbor Laboratory; Cold Spring Harbor, N.Y. (1988), Chapter 6. Antibodies that recognize and bind fragments of Cripto protein are also contemplated, provided that the antibodies are specific for Cripto polypeptides. Antibodies of the invention can be produced using any method well known and routinely practiced in the art.

In one embodiment, the invention provides an antibody that specifically binds to an epitope in the ligand/receptor binding domain of Cripto. Antibody specificity is described in greater detail below. However, it should be emphasized that antibodies that can be generated from other polypeptides that have previously been described in the literature and that are capable of fortuitously cross-reacting with Cripto (e.g., due to the fortuitous existence of a similar epitope in both polypeptides) are considered "cross-reactive" antibodies. Such cross-reactive antibodies are not antibodies that are "specific" for Cripto. The determination of whether an antibody specifically binds to an epitope of Cripto is made using any of several assays, such as Western blotting assays, that are well known in the art. For identifying cells that express Cripto and also for modulating Cripto ligand/receptor binding activity, antibodies that specifically bind to an extracellular epitope of the Cripto protein (i.e., portions of the Cripto protein found outside the cell) are particularly useful.

In one embodiment, the invention provides a cell-free composition comprising polyclonal antibodies, wherein at least one of the antibodies is an antibody of the invention specific for Cripto. Antisera isolated from an animal is an exemplary composition, as is a composition comprising an antibody fraction of an antisera that has been resuspended in water or in another diluent, excipient, or carrier.

In another embodiment, the invention provides monoclonal antibodies. Monoclonal antibodies are highly specific, being directed against a single antigenic site. Further in contrast to polyclonal preparations which typically include different antibodies directed against different epitopes, each monoclonal antibody is directed against a single determinant on the antigen. Monoclonal antibodies are useful to improve selectivity and specificity of diagnostic and analytical assay methods using antigen-antibody binding. Another advantage of monoclonal antibodies is that they are synthesized by a hybridoma culture, uncontaminated by other immunoglobulins. Hybridomas that produce such antibodies are also intended as aspects of the invention.

In still another related embodiment, the invention provides an anti-idiotypic antibody specific for an antibody that is specific for Cripto. For a more detailed discussion of anti-idiotypic antibodies, see, e.g., U.S. Pat. Nos. 6,063,379 and 5,780,029.

It is well known that antibodies contain relatively small antigen binding domains that can be isolated chemically or by recombinant techniques. Such domains are useful Cripto binding molecules themselves, and also may be reintroduced into human antibodies, or fused to a chemotherapeutic or polypeptide. Thus, in still another embodiment, the invention provides a polypeptide comprising a fragment of a Cripto-specific antibody, wherein the fragment and associated molecule, if any, bind to the Cripto. By way of non-limiting example, the invention provides polypeptides that are single chain antibodies and CDR-grafted antibodies. For a more detailed discussion of CDR-grafted antibodies, see, e.g., U.S. Pat. No. 5,859,205.

In another embodiment, non-human antibodies may be humanized by any of the methods known in the art. Humanized antibodies are useful for in vivo therapeutic applications. In addition, recombinant "humanized" antibodies may be synthesized. Humanized antibodies are antibodies initially derived from a nonhuman mammal in which recombinant DNA technology has been used to substitute some or all of the amino acids not required for antigen binding with amino acids from corresponding regions of a human immunoglobulin light or heavy chain. That is, they are chimeras comprising mostly human immunoglobulin sequences into which the regions responsible for specific antigen-binding have been inserted (see, e.g., PCT patent application WO 94/04679). Animals are immunized with the desired antigen, the corresponding antibodies are isolated and the portion of the variable region sequences responsible for specific antigen binding are removed. The animal-derived antigen binding regions are then cloned into the appropriate position of the human antibody genes in which the antigen binding regions have been deleted. Humanized antibodies minimize the use of heterologous (inter-species) sequences in antibodies for use in human therapies, and are less likely to elicit unwanted immune responses. Primatized antibodies can be produced similarly using primate (e.g., rhesus, baboon and chimpanzee) antibody genes. Further changes can then be introduced into the antibody framework to modulate affinity or immunogenicity. See, e.g., U.S. Pat. Nos. 5,585,089, 5,693,761, 5,693,762, and 6,180,370.

Another embodiment of the invention includes the use of human antibodies, which can be produced in nonhuman animals, such as transgenic animals harboring one or more human immunoglobulin transgenes. Such animals may be used as a source for splenocytes for producing hybridomas, as is described in U.S. Pat. No. 5,569,825, WO00076310, WO00058499 and WO00037504 and incorporated by reference herein.

Signal Modulation

In another embodiment, the antibodies of the invention bind to Cripto, and modulate Cripto signaling or Cripto-protein interactions. Over-expression of Cripto activity can lead to a de-differentiated state promoting mesenchymal cell characteristics, increased proliferation, and cell migration (Salomon et al., BioEssays 21: 61-70, 1999; Ciardiello et al., Oncogene 9: 291-298, 1994; and Baldassarre et al., Int. J. Cancer 66:538-543, 1996), phenotypes associated with cell transformation seen in neoplasia.

One method of testing the activity of anti-Cripto antibodies and their ability to modulate Cripto signaling is with an F9-Cripto knock-out (KO) cell line (Minchiotti at al., Mech. Dev. 90: 133-142, 2000). Cripto stimulates smad2 phosphorylation and the transcription factor FAST in Xenopus embryos, and the activity of the transcription factor FAST can be monitored by measuring the luciferase activity from a FAST regulatory element-luciferase reporter gene (Saijoh et al., Mol. Cell 5:35-47, 2000). F9-Cripto KO cells are deleted for the Cripto gene and are thus null for Cripto and Cripto-dependent signaling (Minchiotti at al., Mech. Dev. 90: 133-142, 2000). Cripto signaling can be assessed in the F9 Cripto KO cells by transfecting in Cripto, FAST, and the FAST regulatory element-luciferase gene construct. No Cripto dependent FAST luciferase activity will be seen in these cell lines unless Cripto cDNA, and FAST cDNA is transfected into them. Antibodies capable of blocking Cripto-dependent Nodal signaling are antibodies that block Cripto signaling function.

Other assays capable of measuring the activity of Cripto can be employed by those of skill in the art, such as a growth in soft agar assay (see Example 4 below). The ability of cells to grow in soft agar is associated with cell transformation and the assay is a classical in vitro assay for measuring inhibition of tumor cell growth. Other assays useful in determining inhibition of activity include in vitro assays on plastic, and the like.

Therapeutic Uses

Antibodies of the invention are also useful for, therapeutic purposes, such as modulation of tumor cell growth, diagnostic purposes to detect or quantitate Cripto, and purification of Cripto.

In one embodiment of the invention, antibodies are provided which are capable of binding specifically to Cripto and which modulate growth of tumor cells in a patient. In one embodiment, the tumor cells are testicular, breast, testicular, colon, lung, ovary, bladder, uterine, cervical, pancreatic, and stomach tumor cells.

In another embodiment, antibodies are provided which are capable of binding specifically to Cripto and which modulate growth of tumor cells which overexpress Cripto. In one embodiment, the tumor cells are cell lines which overexpress Cripto, such as cell lines derived from breast, testicular, colon, lung, ovary, bladder, uterine, cervical, pancreatic, and stomach cancer.

Anti-Cripto antibodies may be screened for in vivo activity as potential anticancer agents following standard protocols used by those of skill in the art, as illustrated in Example 4 below. Example of such protocols are outlined by the National Cancer Institute (NCI) in their "in vivo cancer models screening" protocols, NIH publication number 84-2635 (February 1984).

In another embodiment of the invention, the antibodies of the invention are used to treat a patient having a cancerous tumor.

The antibodies of the present invention can be combined with a pharmaceutically acceptable excipient and administered in a therapeutically effective dose to the patient. For a discussion of methods of inhibiting growth of tumors, see, e.g., U.S. Pat. No. 6,165,464.

Also contemplated are methods of treating a subject suffering from a disorder associated with abnormal levels (i.e. elevated or depleted) of Cripto wherein the method comprises administering to the subject an effective amount of an antibody that specifically binds to an epitope in the ligand/receptor binding domain of Cripto, including but not limited to where the epitope is in an EGF-like domain or a cys-rich domain of Cripto.

Also contemplated are methods of treating a subject suffering from a disorder associated with abnormal levels (i.e. elevated or depleted) of Cripto wherein the method comprises administering to the subject an effective amount of an antibody which specifically forms a complex with Cripto and is directed to the epitope to which an antibody selected from the group consisting of A6C12.11, A6F8.6 (ATCC ACCESSION NO. PTA-3318), A7H1.19, A8F1.30, A8G3.5 (ATCC ACCESSION NO. PTA-3317), A8H3.1 (ATCC ACCESSION NO. PTA-3315), A8H3.2, A19A10.30, A10B2.18 (ATCC ACCESSION NO. PTA-3311), A27F6.1 (ATCC ACCESSION NO. PTA-3310), A40G12.8 (ATCC ACCESSION NO. PTA-3316), A2D3.23, A7A10.29, A9G9.9, A15C12.10, A15E4.14, A17A2.16, A17C12.28, A17G12.1 (ATCC ACCESSION NO. PTA-3314), A17H6.1, A18B3.11 (ATCC ACCESSION NO. PTA-3312), A19E2.7, B3F6.17 (ATCC ACCESSION NO. PTA-3319), and B6G7.10 (ATCC ACCESSION NO. PTA-3313) is directed.

Diagnosis via detection of Cripto is readily accomplished through standard binding assays using the novel antibodies of the invention, allowing those of skill in the art to detect the presence of Cripto specifically in a wide variety of samples, cultures, and the like.

Kits comprising an antibody of the invention for any of the purposes described herein are also comprehended. In general, a kit of the invention also includes a control antigen for which the antibody is immunospecific. Embodiments include kits comprising all reagents and instructions for the use thereof.

Additional features of the invention will be apparent from the following illustrative Examples.

EXAMPLES

Example 1

Expression and Purification of Cripto

An expression plasmid designated pSGS480 was constructed by sub-cloning a cDNA encoding human Cripto amino acids residues 1 to 169 of Cripto [amino acids 1-169 of SEQ ID NO: 1], fused to human IgG$_1$ Fc domain (i.e., "CR (del C)-Fc") into vector pEAG1100. For a more detailed description of this vector, see copending U.S. Patent Application Ser. No. 60/233,148, filed Sep. 18, 2000. The vector pEAG1100 is a derivative of GIBCO-BRL Life Technologies plasmid pCMV-Sport-betagal, the use of which in CHO transient transfections was described by Schifferli et al., 1999, Focus 21: 16. It was made by removing the reporter gene beta-galactosidase NotI fragment from the plasmid pCMV-Sport-Betagal (catalog number 10586-014) as follows: The plasmid was digested with NotI and EcoRV, the 4.38 kb NotI vector backbone fragment was gel-purified and ligated. Ligated DNA was transformed into competent *E. coli* DH5alpha. pEAG1100 was isolated as a plasmid containing the desired recombinant from an isolated single colony. The sequence of pEAG1100 spanning the promoter, polylinker, and transcription termination signal was confirmed.

Plasmid pSGS480 was transiently transfected into CHO cells and the cells were grown at 28° C. for 7 days. The presence of CR(del C)-Fc protein in these cells and the conditioned media was examined by Western blot analysis. For Western blot analysis, conditioned media and cells from Cripto transfected cells were subjected to SDS-PAGE on 4-20% gradient gels under reducing conditions, transferred electrophoretically to nitrocellulose, and the Cripto fusion protein was detected with a rabbit polyclonal antiserum raised against a Cripto 17-mer peptide (comprising residues 97-113 of SEQ ID NO: 1)-keyhole limpet hemocyanin conjugate. After centrifugation to remove the cells, Western blot analysis showed that the CR(del C)-Fc protein was efficiently secreted into the conditioned media (supernatant). The supernatant was applied to a Protein A-Sepaharose (Pharmacia), and bound protein was eluted with 25 mM sodium phosphate pH 2.8, 100 mM NaCl. The eluted protein was neutralized with 0.5 M sodium phosphate at pH 8.6, and analyzed for total protein content from absorbance measurements at 240-340 nm, and for purity by SDS-PAGE. The eluted protein was filtered through a 0.2 micron filter, and stored at −70° C.

Example 2

Generation and Screening of Antibodies

The eluted CR(del C)-Fc protein is injected into mice, and standard hybridoma techniques known to those of skill in the art are used to generate monoclonal antibodies.

A. Generation of Antibodies

Particularly, female Robertsonian mice (Jackson Labs) were immunized intraperitoneally with 25 μg of purified human CR del C-Fc emulsified with complete fruend's adjuvant (GibcoBRL #15721-012). They were boosted two times intraperitoneally with 25 μg of CR del C-Fc emulsified with incomplete freunds's adjuvant (GibcoBRL #15720-014) and once on Protein A beads. The sera were screened and 3 weeks after the last boost, the mouse with the best titer was boosted intraperitoneally with 50 μg soluble CR del C-Fc three days before fusion. The mouse was boosted intravenously with 50 μg CR del C-Fc the day before fusion. The mouse spleen cells were fused with FL653 myeloma cell at a 1spleen:6 myeloma ratio and were plated at 100,000, 33,000and 11,000 cells per well into 96 well tissue culture plates in selection media. Wells positive for growth were screened by FACS and ELISA a week later. Two fusions were performed.

B. Screening of Antibodies

Supernatants resulting from the first or second fusion were screened first on ELISA plates for recognition of Cripto del C and/or Cripto EGF-like domain proteins. A control fusion protein (LT-beta receptor-Fc) was coated on ELISA plates to discard monoclonal antibodies that recognized the human Fc epitope. The ELISA was performed as described below in section C. In the first fusion, primary supernatants were also screened for their ability to recognize cell surface Cripto protein on the testicular tumor cell line, NCCIT by FACS. In the case of the second fusion, the ability of supernatants to recognize Cripto on two tumor cell lines, NCCIT and the breast cancer line, DU4475 by FACs was analyzed. Secondary screens included testing the monoclonal antibody supernatant's ability to recognize cell surface Cripto on a panel of tumor cell lines (see Tables 1 and 2 for results), ability of monoclonal antibodies to recognize human Cripto immunohistochemically on human breast and colon tumor tissue sections, ability of monoclonal antibodies to block in Cripto-Nodal signalling assay, ability to block growth of tumor cell lines on plastic or in soft agar assays, and ability to internalize cell surface Cripto.

C. ELISA

The ELISA assays were performed as follows:

Materials:
  Plates: Costar high-binding Easy-wash 96W plates (07-200-642)
  2' antibody: Pierce Gt anti-Ms IgG (H+L)-HRP (P131430)
  Substrate: Pierce TMB Substrate Kit (34021)
  Stop solution: 1N H2SO4

Buffers:
  Binding buffer: 0.1 M NaHPO4 pH 9.0
  Blocking buffer: PBS+10% Donor Calf Serum
  Wash buffer: PBS+0.1% tween-20

Antigens CR-del-C-Fc and CR-EGF-fc, control hu IgG1 fusion protein were diluted in binding buffer to 500 ng/ml. 100 μl were added per well and incubated for 1 hr at 37° C. or overnight at 4° C. The liquid was decanted and the plate inverted and blotted until dry. 250 μl/well blocking buffer was then added, followed by incubation for 30 min. at 37° C. Again, the liquid was decanted and the plate inverted and blotted until dry. Supernatants were diluted 1:50 in wash buffer, and plated at 50 μl/well, followed by incubation for 1 hour at room temperature. Plates were washed 3× vigorously with 250 μl /well wash buffer. Then 100 μl/well 2' antibody diluted in wash buffer at 1:10,000 was added, followed by incubation for 30 min. at room temperature. Plates were then washed 3× vigorously with 250 μl/well wash buffer, then substrate added at 100 μl/well. Color was permitted to develop until sufficiently dark, then 100 μl/well stop solution was added and the plates read for absorbance at 450 nm.

D. Flow Cytometry

Cripto positive cell lines may be used to assay the monoclonal antibodies for binding to Cripto using cell surface staining and flow cytometry as follows:

Release cells from T162 flasks with 2 ml PBS⁻ with 5 mM EDTA, 10 min., 37° C. Bring up to 20 ml with media with serum, pipetting up and down several times to unclump cells. Spin at 1200 rpm for 5 minutes. Wash cells with 5-10 ml 4° C. PBS with 0.1% BSA (wash buffer). Spin at 1200 rpm for 5 minutes. Resuspend at $4\times10^6$-$10^7$/ml in wash buffer. Keep on ice.

Prepare antibodies for staining. Purified antibodies are diluted to 1-10 μg/ml in wash buffer. Add 50 μl of cells to a 96-well Linbro V bottomed plate (ICN 7632105). Plate one well of cells for each control for each cell line to be analyzed, including cells for no antibody, 2° antibody only, hybridoma media, positive control antibody supernatant, if available, or purified, and an IgG subclass control (if using purified antibodies).

Plate one well of cells for each experimental sample for each cell line to be analyzed. Spin plate, 1200 rpm for 5 minutes, using a table top centrifuge at 4° C. Flick out buffer by inverting the plate and shaking until the liquid is substantially discarded. Add 40-50 μl of antibodies (or wash buffer for the no-antibody and 2° antibody-only control wells) to wells. Incubate at least 30 min.-1 hour at 4° C. Spin plate, 1200 rpm for 5 minutes. Flick out antibody solutions. Wash wells twice with 200 μl wash buffer per well, spinning after each wash. Flick out buffer.

Resuspend cells in each well in 50 μl of 1:200 dilution (in wash buffer) of R-PE tagged goat anti-mouse IgG, Fc Specific (Jackson Immunoresearch Laboratories Cat# 115-116-071). Incubate 20 min, 4° C., in the dark. Add 150 μl wash buffer to cells in each well. Spin plate at 1200 rpm for 5 minutes. Wash once with 200 μl wash buffer per well. Resuspend cells in 150 μl 1% PFA in PBS. Transfer contents of each well to separate tubes (5 ml Falcon polystyrene round bottomed tube-352052). Wrap tubes in tin foil.

The contents of the tubes are then read by flow cytometry.

The results of a two screenings of monoclonal antibodies produced by this method yielded the following results, summarized in Tables 1 and 2 below, wherein the first column provides the designated names for the hybridoma subclones, the next two columns show the results of ELISA screens, and the remaining columns show flow cytometry analysis results on four cripto-positive cell lines. The results are given in units of mean fluorescent index (MFI).

TABLE 1

Anti-Cripto Monoclonal Antibody Characterization

| Hybridoma Subclone | ATCC deposit no. | ELISA Cripto delC Sups | ELISA Cripto EGFlike domain Sups | DU4475 MFI | NCCIT MFI | GEO MFI | HT3 MFI |
|---|---|---|---|---|---|---|---|
| Control-ELISA | | 0.06 | 0.07 | | | | |
| Control-MouseIg | | | | 14 | 9 | 37 | 18 |

TABLE 1-continued

Anti-Cripto Monoclonal Antibody Characterization

| Hybridoma Subclone | ATCC deposit no. | ELISA Cripto delC Sups | ELISA Cripto EGFlike domain Sups | DU4475 MFI | NCCIT MFI | GEO MFI | HT3 MFI |
|---|---|---|---|---|---|---|---|
| A6C12.11 | | 2.21 | 0.07 | 11 | 35 | 29 | 8 |
| A6F8.6 | PTA-3318 | 2.32 | 0.08 | 11 | 50 | 29 | 10 |
| A7H1.19 | | 2.14 | 0.09 | 14 | 34 | 27 | 12 |
| A8F1.30 | | 2.15 | 0.1 | 17 | 27 | 32 | 28 |
| A8G3.5 | PTA-3317 | 2.39 | 0.09 | 9 | 30 | 25 | 15 |
| A8H3.1 | PTA-3315 | 2.4 | 1.7 | 9 | 44 | 23 | 10 |
| A8H3.2 | | 2.54 | 0.07 | 13 | 13 | 16 | 14 |
| A19A10.30 | | 2.02 | 0.09 | 9 | 40 | 20 | 10 |
| A10B2.18 | PTA-3311 | 2.36 | 0.07 | 40 | 63 | 100 | 43 |
| A27F6.1 | PTA-3310 | 2.28 | 1.19 | 9 | 44 | 26 | 17 |
| A40G12.8 | PTA-3316 | 2.27 | 1.59 | 10 | 47 | 26 | 16 |

TABLE 2

Anti-Cripto Monoclonal Antibody Characterization

| Hybridoma Subclone | ATCC deposit no. | ELISA Cripto delC | ELISA Cripto EGFlike domain | DU4475 MFI | NCCIT MFI | GEO MFI | HT3 MFI |
|---|---|---|---|---|---|---|---|
| Control-ELISA | | 0.05 | 0.05 | | | | |
| Control-MouseIg | | | | 10 | 6 | 4 | 6 |
| A2D3.23 | | 0.93 | 0.90 | 73 | 138 | 37 | 27 |
| A7A10.29 | | 1.37 | 0.07 | 75 | 83 | 33 | 83 |
| A9G9.9 | | 1.39 | 0.07 | 52 | 62 | 32 | 82 |
| A15C12.10 | | 1.42 | 0.06 | 46 | 55 | 25 | 93 |
| A15E4.14 | | 1.38 | 0.06 | 50 | 63 | 23 | 95 |
| A17A2.16 | | 1.40 | 0.06 | 76 | 97 | 41 | 81 |
| A17C12.28 | | 0.96 | 0.97 | 6 | 16 | 3 | 22 |
| A17G12.1 | PTA-3314 | 1.30 | 1.37 | 61 | 66 | 28 | 78 |
| A17H6.1 | | 1.38 | 0.05 | 35 | 30 | 5 | 28 |
| A18B3.11 | PTA-3312 | 1.36 | 1.38 | 50 | 42 | 33 | 65 |
| A19E2.7 | | 1.40 | 0.06 | 53 | 59 | 26 | 99 |
| B3F6.17 | PTA-3319 | 1.37 | 0.06 | 77 | 51 | 39 | 89 |
| B6G7.10 | PTA-3313 | 1.38 | 1.40 | 28 | 22 | 22 | 56 |
| B11H8.4 | | 1.41 | 0.06 | 59 | 101 | 39 | 107 |
| B12C12.5 | | 1.10 | 1.04 | 27 | 14 | 23 | 59 |
| B15A2.6 | | 1.40 | 0.06 | 36 | 44 | 22 | 59 |
| C4A2.16 | | 1.40 | 0.06 | 24 | 36 | 22 | 65 |

Example 3

Null Cell Assay for Inhibition of Cripto Signaling

The following describes an F9 Cripto null cell signaling assay used to assess inhibition of Cripto signaling.

Day 0 Coat 6 welled plates with 0.1% gelatin 2 ml/well at 37° C. for 15 min.

Seed cells at $6 \times 10^5$ F9 CRIPTO NULL cells per well.

Day 1 Transfection:

Each of the following samples is added to 300 µl Opti-Mem1 to yield Solution A for each sample:

Sample 1: 0.5 µg $(N_2)_7$ luciferase FAST reporter cDNA plus 1.5 µg empty vector cDNA.

Sample 2: 0.5 µg $(N_2)_7$ luciferase, 0.5 µg FAST, and 1 µg empty vector cDNAs.

Sample 3: 0.5 µg $(N_2)_7$ luciferase, 0.5 µg Cripto ADD 0.5 FAST, and 10.5 µg empty vector cDNAs.

Sample 4: 0.5 µg $(N_2)_7$ luciferase, 0.5 µg Cripto, 0.5 FAST, and 0.5 µg empty vector cDNAs Sample 5: 0.5 µg $(N_2)_7$ luciferase, 0.5 µg Cripto, 0.5 FAST, and 0.5 µg empty vector cDNAs.

Sample 6: 0.5 µg $(N_2)_7$ luciferase, 0.5 µg Cripto, 0.5 FAST, and 0.5 µg empty vector cDNAs.

Sample 7: 0.5 µg $(N_2)_7$ luciferase, 0.5 µg Cripto, 0.5 FAST, and 0.5 µg empty vector cDNAs.

Sample 8: 0.5 µg $(N_2)_7$ luciferase, 0.5 µg Cripto, 0.5 FAST, and 0.5 µg empty vector cDNAs.

Sample 9: 0.5 µg $(N_2)_7$ luciferase, 0.5 µg Cripto, 0.5 FAST, and 0.5 µg empty vector cDNAs.

Solution B comprises 30 µl of Lipofectamine plus 270 µl of OptiMem1.

For each sample, mix solution A and solution B together. Incubate 45 minutes at room temperature. Rinse wells with 2 m/well of OptiMem1. Aspirate just before next step.

Add 2.4 ml of OptiMem1 to each mixture of solutions A+B, mix, add 1.5 ml/well to duplicate wells. Incubate 5 hours at 37° C. Add 1.5 ml/well of DMEM+20% FCS, 2 mM Gln, P/S to wells which received samples 1-3. Add anti-Cripto antibodies as follows: Sample 4 wells: A27F6.1, 10

μg/ml; Sample 5 wells: A27F6.1, 2 μg/ml; Sample 6 wells: A40G12.8; 10 μg/ml, Sample 7 wells: A40G12.8 2 μg/ml; Sample 8 wells: A10B2.18, 10 g/ml; Sample 9 wells: A10B2.18, 2 μg/ml.

Day 2 Remove media, wash cells with PBS, 2 ml/well. Add DMEM+0.5% FCS, 2 mM Gln, P/S with the same amounts of Cripto antibodies as the previous day, to the same wells.

Day 3 Develop luciferase signal. Wash wells with PBS+ $Ca^{2+}$ and $Mg^{2+}$, 2 ml/well. Use LucLite kit, Packard cat# 6016911. Bring buffer and substrate to room temperature. Dim lights. Reconstitute substrate with 10 ml of buffer. Dilute 1:1 with PBS+$Ca^{2+}$ and $Mg^{2+}$. Aspirate wells. Quickly add 250 μl of diluted substrate per well using a repeat pipettor. Swirl solution and transfer 200 μl to wells of a 96 welled white opaque bottom plate, Falcon 35-3296. Read plate on luminometer using Winglow, exporting data to Excel.

The results of this assay are summarized below in Table 3.

TABLE 3

Cripto Signaling Assay: Inhibition with Anti-Cripto Monoclonal Antibodies

| cDNAs transfected | Anti-Cripto Antibody | Relative Luminescent Units |
|---|---|---|
| $(N_2)_7$ luc | none | 123 |
| $(N_2)_7$ luc, FAST | none | 259 |
| $(N_2)_7$ luc, FAST, Cripto | none | 3091 |
| $(N_2)_7$ luc, FAST, Cripto | A27F6.1 10 μg/ml | 1507 |
| $(N_2)_7$ luc, FAST, Cripto | A27F6.1 2 μg/ml | 2297 |
| $(N_2)_7$ luc, FAST, Cripto | A40G12.8 10 μg/ml | 1213 |
| $(N_2)_7$ luc, FAST, Cripto | A40G12.8 2 μg/ml | 2626 |
| $(N_2)_7$ luc, FAST, Cripto | A10B2.18 10 μg/ml | 3466 |
| $(N_2)_7$ luc, FAST, Cripto | A10B2.18 2 μg/ml | 3103 |

Example 4

Assay for In Vitro Inhibition of Tumor Cell Growth

Inhibition of Cripto Signaling may also be assayed by measuring the growth of GEO cells in soft agar. See, e.g., Ciardiello et al., Oncogene. 1994 January;9(1):291-8; Ciardiello et al., Cancer Res. 1991 Feb. 1;51(3):1051-4.

First, melt 3% bactoagar. Keep at 42° C. in a water bath. Then, mix 3% bactoagar solution with prewarmed complete media to make a solution of 0.6% bactoagar, keeping at 42° C. Plate 4 mls of the solution in a 6 cm dish and let cool for at least 30 minutes to form the bottom agar layer. Trypsinize GEO cells and resuspend to $10^5$ cells/ml in complete media. Add antibodies to be assayed, or controls, to the cell suspensions, titrating antibodies from 20 μg to 1 μg. Mix equal volumes of the GEO cell suspensions and 0.6% bactoagar and overlay 2 mls on top of the bottom agar layer. Let cool for at least 1 hour. Incubate for 14 days at 37° C. in $CO_2$ incubator. Count colonies visible without the use of a microscope. The absence of colonies, as compared to negative controls, indicates that the antibody tested inhibits in vitro tumor cell growth.

This assay was used to yield the results shown in Table 4, for the antibodies A27F6.1 and B6G7.10, both of which demonstrate the ability to decrease growth of GEO cell colonies.

TABLE 4

Results of growth in soft agar assay

| Antibody | Average number of colonies |
|---|---|
| none | 109.0 |
| none | 104.3 |
| A27.F6 20 μg/ml | 82.0 |
| A27F6.1 10 μg/ml | 78.3 |
| A27F6.1 5 μg/ml | 79.0 |
| A27F6.1 1 μg/ml | 108.7 |
| B6G7.10 20 μg ml | 102.3 |
| B6G7.10 10 μg/ml | 71.7 |

Example 5

Assay for In Vivo Inhibition of Tumor Cell Growth

To assess the inhibition of tumor cell growth, a human tumor cell line is implanted subcutaneously in athymic nude mice and the effects of the antibodies of the invention are observed, with and without additional chemotherapeutic treatments which may provide synergistic or additive effects on tumor inhibition.

This assay may be performed alternatively using different tumor cell lines, such as, for example, GEO (a well differentiated human colon cancer in-vitro cell line, is obtained from the American Tissue Type Collection (ATCC)), DU-4475 (a breast cancer in-vitro cell line obtained from the ATCC), NCCIT (a testicular tumor cell line obtained from ATCC), or others known in the art. One example of such assays is as follows:

Animals are individually marked by ear punches. The GEO cell line is passed in-vitro or in-vivo for 1-4 passages. Animals are implanted with GEO cells subcutaneously in the right flank area. The following groups of animals may be used:

| Group # | Treatment | # of Mice |
|---|---|---|
| 1. | Saline Control, 0.2 ml/mouse, i.p. three times weekly (M, W, F) | 20 |
| 2. | mAb, low dose, i.p. | 10 |
| 3. | mAb, middle dose, i.p. | 10 |
| 4. | mAb, high dose, i.p. | 10 |
| 5. | 5-FU, 30 mg/kg/inj, i.p., 3 Rx/wk (M, W, F) | 10 |
| 6. | Cisplatin, 2 mg/kg/inj, s.c., 3 Rx/wk (M, W, F) | 10 |
| 7. | Adriamycin, 1.6 mg/kg/inj, i.p., 3 Rx/wk (M, W, F) | 10 |
| 8. | Irinotecan, 10 mg/kg/inj., i.p., 5 Rx/wk (M-F) | 10 |
| 9. | mAb, low dose, i.p. + 5-FU (intermediate dose) | 10 |
| 10. | mAb, middle dose, i.p. + 5-FU (intermediate dose) | 10 |
| 11. | mAb, high dose, i.p. + 5-FU (intermediate dose) | 10 |
| 12. | mAb, low dose, i.p. + Cisplatin (intermediate dose) | 10 |
| 13. | mAb, middle dose, i.p. + Cisplatin (intermediate dose) | 10 |
| 14. | mAb, high dose, i.p. + Cisplatin (intermediate dose) | 10 |
| 15. | mAb, low dose, i.p. + Adriamycin (intermediate dose) | 10 |
| 16. | mAb, middle dose, i.p. + Adriamycin (intermediate dose) | 10 |
| 17. | mAb, high dose, i.p. + Adriamycin (intermediate dose) | 10 |
| 18. | mAb, low dose, i.p. + Irinotecan (intermediate dose) | 10 |
| 19. | mAb, middle dose, i.p. + Irinotecan (intermediate dose) | 10 |
| 20. | mAb, high dose, i.p. + Irinotecan (intermediate dose) | 10 |

Day 0: Implant tumor, record initial body weight of animals.

Day 1: Initiate treatments as indicated above.

Day 5: Begin tumor size and body weight measurements and continue two times weekly until termination of experiment.

Initial body weight, tumor size and body weight measurements, histology at sacrifice, and immunohistochemistry analysis on tumors are examined, analyzing for Cripto expression, tumor growth, and inhibition thereof.

Example 6

In Vivo Xenograft Tumor Model—Cys-rich Blocking Anti-Cripto Antibody

To assess the response of an NCCIT, a human testicular carcinoma cell line was implanted subcutaneously with an antibody which binds to a cys-rich domain of Cripto. The experimental methods are listed below. The results are shown in FIG. 1.

| Methods and Materials | |
|---|---|
| Animals: | Athymic nude male mice were used. Animals were individually numbered by ear punches. |
| Tumor: | NCCIT, mediastinal mixed germ cell human testicular carcinoma in-vitro cell line originally obtained from the American Tissue Type Collection. Cell line was passed in-vitro for six passages in RPMI-1640/10% FBS without antibiotics. Animals implanted subcutaneously with $5 \times 10^6$ cells/0.2 ml matrigel on the animals right flank. |

| Group # | Treatment | # of Mice |
|---|---|---|
| 1 | Vehicle Control, (25 mM sodium phosphate, 100 mM sodium chloride, pH 7.2), 0.2 ml/mouse, i.p., Q14D Treatments begin on day-1 | 20 |
| 2. | A8G3.5, 1 mg/kg/inj, i.p., Q14D Treatments begin on day-1 | 10 |
| 3. | A8G3.5, 3 mg/kg/inj, i.p., Q14D Treatments begin on day-1 | 10 |
| 4. | A8G3.5, 10 mg/kg/inj, i.p., Q14D Treatments begin on day-1 | 10 |
| 5. | Cis-platinum, 2 mg/kg/inj, s.c., 3x/wk (M, W, F) for 6 treatments | 10 |

Treatments began on day 1

Testing schedule

| | |
|---|---|
| Day −1: | Randomized mice into control and treatments groups. Recorded initialbody weight of animals. Administered first treatments to antibody groups. Dosing solutions were made. Treatments were blinded to the technicians until the assay was terminated. |
| Day 0: | Implanted tumor. Ran bacterial cultures on the tumor implanted into mice. |
| Day 1: | Administered first treatment to the positive chemotherapeutic group. |
| Day 4: | Recorded initial tumor size measurements for tumor baseline on matrigel. Continued to record tumor size and body weights on mice 2x/week. Monitored the study daily and made notations of any unusual observation on animals. |
| Endpoints: | Initial body weight Tumor size and body weight measurements |

Example 7

In Vivo Xenograft Tumor Model—EGF-like Domain Blocking Anti-Cripto Antibody

Figure 2:
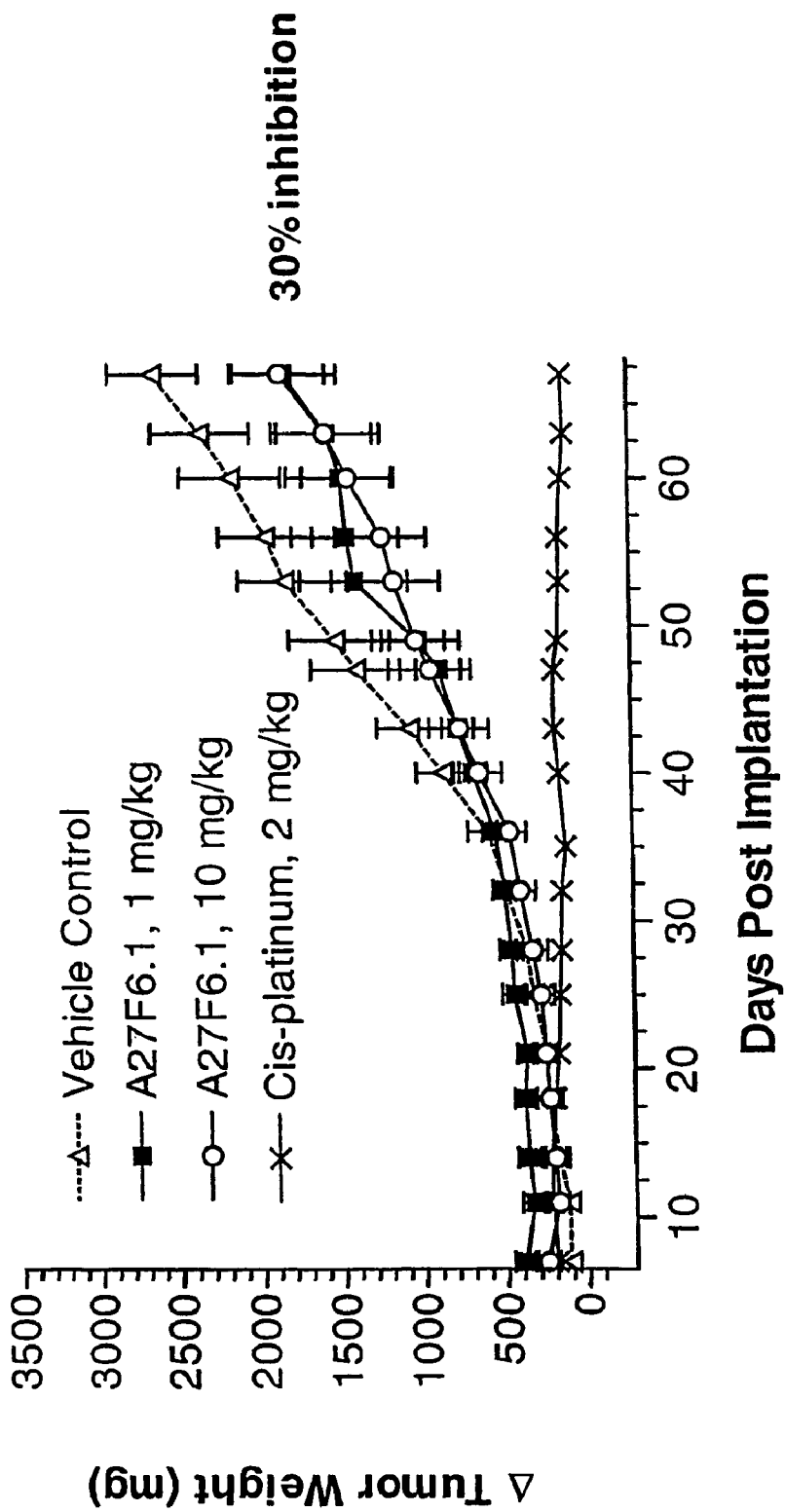
FIG. 2 shows the response of the NCCIT, human testicular carcinoma cell line, to anti-EGF blocking Cripto mAb A27F6.1.

To assess the response of an NCCIT, a human testicular carcinoma cell line was implanted subcutaneously with an antibody which binds to a EGF-like domain of Cripto. The experimental methods are listed below. The results are shown in FIG. 2.

| Methods and Materials: | |
|---|---|
| Animals: | Athymic nude male mice were used. Animals were individually numbered by ear punches. |
| Tumor: | NCCIT, mediastinal mixed germ cell human testicular carcinoma in-vitro cell line originally obtained from the American Tissue Type Collection. Cell line was passed in-vitro for eight passages in RPMI-1640/10% FBS without antibiotics. Animals implanted subcutaneously with $5 \times 10^6$ cells/0.2 ml matrigel on the animals right flank. |

| Group # | Treatment | # of Mice |
|---|---|---|
| 1. | Vehicle Control, (25 mM sodium phosphate, 100 mM sodium chloride, pH 7.2), 0.2 ml/mouse, i.p., Q14D Treatments begin on day-1 | 18 |
| 2. | A27F6.1, 1 mg/kg/inj, i.p., Q14D Treatments begin on day-1 with a loading dose of 2.6 mg/kg/mouse | 10 |
| 3. | A27F6.1, 10 mg/kg/inj, i.p., Q14D Treatments begin on day-1 with a loading dose of 21.2 mg/kg/mouse | 10 |
| 4. | Cis-platinum, 2 mg/kg/inj, s.c., 3x/wk (M, W, F) for 6 treatments | 10 |

Treatments began on day 1.

Testing schedule

| | |
|---|---|
| Day −1: | Randomized mice into control and treatments groups. Recorded initial body weight of animals. Administered first treatments to antibody groups. Dosing solutions were made. Treatments were blinded to the technicians until the assay was terminated. |
| Day 0: | Implant tumor. Ran bacterial cultures on the tumors implanted into mice. Bacterial culture were negative for contamination at 24 and 48 hours post sampling. |
| Day 1: | Administered first treatment to the positive chemotherapeutic group. |
| Day 4: | Recorded initial tumor size measurements for tumor baseline on matrigel. Continued to record tumor size and body weights on mice 2 x/week. Monitored the study daily and made notations of any unusual observation on animals. |
| Endpoints: | Initial body weight Tumor size and body weight measurements |

Example 8

Cripto Mabs that Block ALK4 Binding

In order to assess whether Cripto-specific monoclonal antibodies can interfere with Cripto's ability to bind to Alk4, the activin type I receptor, we used flow cytometry analysis using a 293 cell line which stably expresses Alk4. To generate this cell line, 293 cells were cotransfected with a plasmid that expresses Alk4 tagged at the C-terminus with a HA epitope and a plasmid that expresses the drug, puromycin, at a 10:1 ratio. The transfected cells were then selected in puromycin until colonies formed. Colonies were then picked, expanded and then analyzed for Alk4 expression using western blotting analysis for HA. Clone 21 (293-Alk4-21) was found to express high levels of Alk4 compared to control, untransfected 293 cells.

Figure 3:
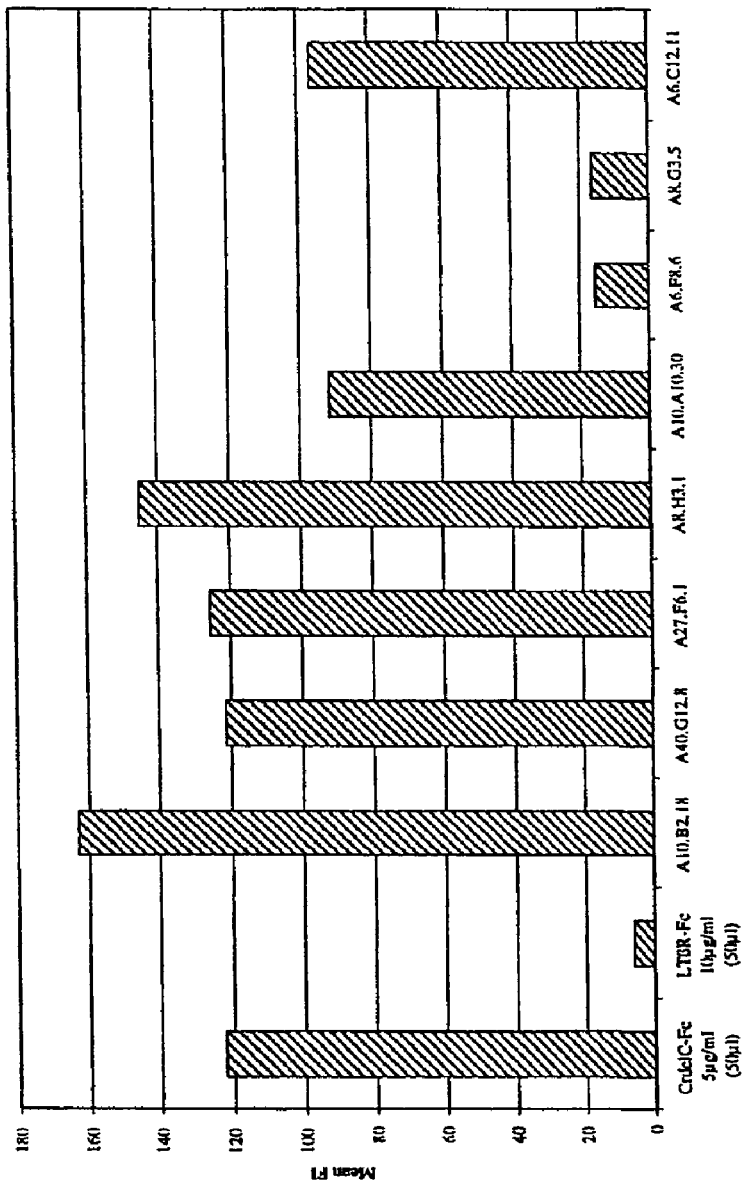
FIG. 3 depicts the results of the FACS analysis showing 293/ALK4 cells binding CR-Fc.

To analyze Cripto-Alk4 binding by flow cytometry, a purified, soluble form of human Cripto (aa 1-169) fused to the Fc portion of human IgG (CrdelC-Fc) was employed. Approximately 5 μg/ml of CrdelC-Fc or control Fc protein was incubated with 3×10[5] 293-Alk4-21 cells on ice for 30 minutes in 50 μl total volume of FACS buffer (PBS with 0.1% BSA). For samples containing anti-Cripto antibodies, 5 μg/ml CrdelC-Fc was preincubated with 50 μg/ml of each Cripto antibody (A10B2.18, A40.G12.8, A27.F6.1, A8.H3.1, A19.A10.30, A6.F8.6, A8.G3.5, A6.C12.11) on ice prior to addition of the cells. The cells were then washed in FACS buffer and the bound Fc protein was detected by incubating the cells with a R-phycoerytherin-conjugated goat anti-human IgG (Fc fragment specific) from Jackson Immunologics. Samples were then washed again, fixed in 1% paraformaldehyde in PBS, and analyzed using standard flow cytometry procedures. The results of the FACS assay are shown in FIG. 3.

Some of the embodiments of the invention described above are outlined below and include, but are not limited to, the following embodiments. As those skilled in the art will appreciate, numerous changes and modifications may be made to the various embodiments of the invention without departing from the spirit of the invention. It is intended that all such variations fall within the scope of the invention.

The entire disclosure of each publication cited herein is hereby incorporated by reference.

We claim:

1. A method of treating a subject having a tumor that over-expresses Cripto comprising administering to the subject a composition comprising a monoclonal antibody that specifically binds to an epitope of Cripto comprised in the domain spanning amino acid residues from amino acid 46 to amino acid 62 of SEQ ID NO:1 or amino acid residues from about amino acid 46 to about amino acid 62 of SEQ ID NO:2 in an effective amount.

2. The method according to claim 1, wherein the subject is human.

3. A method of treating a subject having a tumor that over-expresses Cripto comprising administering to the subject a composition comprising a monoclonal antibody that specifically binds to an epitope of Cripto comprised in the cysteine-rich domain of Cripto spanning from about amino acid residue 114 to about amino acid residue 150 of SEQ ID NO:1 or from about amino acid residue 114 to about amino acid residue 150 of SEQ ID NO:2 in an effective amount.

4. A method of treating a subject having a tumor that over-expresses Cripto comprising administering to the subject a composition comprising a monoclonal antibody which binds specifically to an epitope of Cripto selected from the group of epitopes to which antibodies produced by hybridomas A6F8.6, A8G3.5, A10B2.18 and B3F6.17 bind in an effective amount.

5. The method according to claim 1, wherein the tumor cell is selected from the group consisting of breast, testicular, colon, lung, ovary, bladder, uterine, cervical, pancreatic, and stomach tumors.

6. The method of claim 1, wherein the antibody is a humanized antibody.

7. The method of claim 1, wherein the antibody is a human antibody.

8. A method of inhibiting proliferation of tumor cells that express Cripto in a subject comprising the step of administering to the subject an effective amount of a composition comprising a monoclonal antibody that specifically binds to an epitope of Cripto comprised in the domain spanning amino acid residues from amino acid 46 to amino acid 62 of SEQ ID NO:1 or from about amino acid 46 to anout amino acid 62 of SEQ ID NO:2 and a pharmaceutically acceptable carrier.

9. The method of claim 1, wherein the antibody is an antibody fragment selected from the group consisting of a Fab, a Fab', and a F(ab')2 fragment.

10. The method of claim 1, wherein the antibody is a full length antibody.

11. The method of claim 1, wherein the antibody is a single chain antibody.

12. The method of claim 1, wherein the antibody is conjugated to a chemotherapeutic agent.

13. The method of claim 1, wherein the antibody is administered in combination with a chemotherapeutic agent which is not conjugated to the antibody.

14. The method of claim 12, wherein the chemotherapeutic agent is selected from the group consisting of a tumor-activated prodrug, a radionuclide and a toxin.

15. The method of claim 14, wherein the agent is a maytansinoid.

16. A method of inhibiting proliferation of tumor cells that express Cripto in a subject comprising the step of administering to the subject an effective amount of a composition comprising a monoclonal that specifically binds to an epitope of Cripto comprised in the domain spanning amino acid residues from amino acid 46-62 of SEQ ID NO:1 or amino acid residues from about amino acid 46-62 of SEQ ID NO:2, wherein the antibody is conjugated to a maytansinoid, and a pharmaceutically acceptable carrier.

17. A method of inhibiting proliferation of tumor cells that express Cripto in a subject comprising the step of administering to the subject an effective amount of a composition comprising a monoclonal antibody that binds to Cripto, wherein the antibody is a humanized version of the antibody produced by the hybridoma B3F6.17.

18. A method of inhibiting proliferation of tumor cells that express Cripto in a subject comprising the step of administering to the subject an effective amount of a composition comprising a monoclonal antibody that specifically binds to an epitope of Cripto to which an antibody produced by hybridoma B3F6.17 binds, and a pharmaceutically acceptable carrier.

19. A method of inhibiting proliferation of tumor cells that express Cripto in a subject comprising the step of administering to the subject an effective amount of a composition comprising a monoclonal antibody, wherein the antibody specifically binds to an epitope of Cripto selected from the group of epitopes to which antibodies produced by hybridomas of A27F6.1 and B3F6.17 bind, and is capable of internalizing Cripto.

20. A method of inhibiting proliferation of tumor cells that express Cripto in a subject comprising the step of administering to the subject an effective amount of a composition comprising a monoclonal antibody that specifically binds to an epitope of Cripto comprised in the cysteine-rich domain of Cripto spanning from about amino acid residue 114 to about amino acid residue 150 of SEQ ID NO:1 or from about amino acid residue 114 to about amino acid residue 150 of SEQ ID NO:2, and a pharmaceutically acceptable carrier.

21. A method of inhibiting proliferation of tumor cells that express Cripto in a subject comprising the step of administering to the subject an effective amount of a composition comprising a monoclonal antibody that binds to Cripto, wherein the antibody specifically binds to an epitope of Cripto selected from the group of epitopes to which antibodies produced by hybridomas of A8G3.5, and A6F8.6 bind, and a pharmaceutically acceptable carrier.

22. A method of inhibiting proliferation of tumor cells that express Cripto in a subject comprising the step of administering to the subject an effective amount of a composition comprising a monoclonal antibody that specifically binds to a Cripto amino acid sequence shown in SEQ ID NO: 1 or SEQ ID NO:2 and inhibits the interaction of Cripto and ALK4.

23. A method of inhibiting proliferation of tumor cells that express Cripto in a subject comprising the step of administering to the subject an effective amount of a composition comprising a monoclonal antibody that binds specifically to an epitope of Cripto selected from the group of epitopes to which antibodies produced by hybridomas A6F8.6, A8G3.5, A10B2.18, and B3F6.17 bind, and a pharmaceutically acceptable carrier.

24. A method of inhibiting proliferation of tumor cells that express Cripto in a subject comprising the step of administering to the subject an effective amount of a composition comprising a monoclonal antibody that binds to Cripto, wherein the antibody specifically binds to an epitope of Cripto to which an antibody produced by hybridoma A10B2.18 binds, and a pharmaceutically acceptable carrier.

25. A method of treating a subject having a tumor that over-expresses Cripto comprising administering to the subject a composition comprising a monoclonal antibody that specifically binds to an epitope of Cripto comprised in the domain spanning amino acid residues from amino acid 46-62 of SEQ ID NO: 1 or amino acid residues from about amino acid 46-62 of SEQ ID NO:2, wherein the antibody is conjugated to a maytansinoid, in an effective amount.

26. A method of treating a subject having a tumor that over-expresses Cripto comprising administering to the subject a composition comprising a humanized version of the antibody produced by the hybridoma B3F6.17 in an effective amount.

27. A method of treating a subject having a tumor that over-expresses Cripto comprising administering to the subject a composition comprising a monoclonal antibody that specifically binds to an epitope of Cripto to which an antibody produced by the hybridoma B3F6.17 binds in an effective amount.

28. A method of treating a subject having a tumor that over-expresses Cripto comprising administering to the subject a composition comprising a monoclonal antibody that specifically binds to an epitope of Cripto to which an antibody produced by the hybridoma A10B2.18 binds in an effective amount.

29. A method of treating a subject having a tumor that over-expresses Cripto comprising a monoclonal antibody, wherein the antibody specifically binds to an epitope of Cripto selected from the group of epitopes to which antibodies produced by hybridomas A27F6.1 and B3F6.17 bind, and is capable of internalizing Cripto.

30. A method of treating a subject having a tumor that over-expresses Cripto comprising administering to the subject a composition comprising a monoclonal antibody that specifically binds to an epitope of Cripto selected from the group of epitopes to which antibodies produced by hybridomas A8G3.5, and A6F8.6 bind in an effective amount.

31. A method of treating a subject having a tumor that over-expresses Cripto comprising administering to the subject a composition comprising a monoclonal antibody that specifically binds to a Cripto amino acid sequence shown in SEQ ID NO: 1 or SEQ ID NO: 2 and inhibits the interaction of Cripto and ALK4 in an effective amount.

32. The method according to claim 3, wherein the subject is human.

33. The method according to claim 3, wherein the tumor is selected from the group consisting of breast, testicular, colon, lung, ovary, bladder, uterine, cervical, pancreatic, and stomach tumors.

34. The method of claim 3, wherein the antibody is a humanized antibody.

35. The method of claim 3, wherein the antibody is a human antibody.

36. The method of claim 3, wherein the antibody is an antibody fragment selected from the group consisting of a Fab, a Fab', and a F(ab')2 fragment.

37. The method of claim 3, wherein the antibody is a full length antibody.

38. The method of claim 3, wherein the antibody is a single chain antibody.

39. The method of claim 3, wherein the antibody is administered in combination with a chemotherapeutic agent which is not conjugated to the antibody.

40. The method of claim 3, wherein the antibody is conjugated to a chemotherapeutic agent.

41. The method of claim 40, wherein the chemotherapeutic agent is selected from the group consisting of a tumor-activated prodrug, a radionuclide and a toxin.

42. The antibody of claim 41, wherein the agent is a maytansinoid.

43. The method according to claim 4, wherein the subject is human.

44. The method according to claim 4, wherein the tumor is selected from the group consisting of breast, testicular, colon, lung, ovary, bladder, uterine, cervical, pancreatic, and stomach tumors.

45. The method of claim 4, wherein the antibody is a humanized antibody.

46. The method of claim 4, wherein the antibody is a human antibody.

47. The method of claim 4, wherein the antibody is an antibody fragment selected from the group consisting of a Fab, a Fab', and a F(ab')2 fragment.

48. The method of claim 4, wherein the antibody is a full length antibody.

49. The method of claim 4, wherein the antibody is a single chain antibody.

50. The method of claim 4, wherein the antibody is administered in combination with a chemotherapeutic agent which is not conjugated to the antibody.

51. The method of claim 4, wherein the antibody is conjugated to a chemotherapeutic agent.

52. The method of claim 51, wherein the chemotherapeutic agent is selected from the group consisting of a tumor-activated prodrug, a radionuclide and a toxin.

53. The antibody of claim 52, wherein the agent is a maytansinoid.

54. The method according to claim 8, wherein the subject is human.

55. The method according to claim 8, wherein the tumor cell is selected from the group consisting of breast, testicular, colon, lung, ovary, bladder, uterine, cervical, pancreatic, and stomach tumor cells.

56. The method of claim 8, wherein the antibody is a humanized antibody.

57. The method of claim 8, wherein the antibody is a human antibody.

58. The method of claim 8, wherein the antibody is an antibody fragment selected from the group consisting of a Fab, a Fab', and a F(ab')2 fragment.

59. The method of claim 8, wherein the antibody is a full length antibody.

60. The method of claim 8, wherein the antibody is a single chain antibody.

61. The method of claim 8, wherein the antibody is administered in combination with a chemotherapeutic agent which is not conjugated to the antibody.

62. The method of claim 8, wherein the antibody is conjugated to a chemotherapeutic agent.

63. The method of claim 62, wherein the chemotherapeutic agent is selected from the group consisting of a tumor-activated prodrug, a radionuclide and a toxin.

64. The antibody of claim 63, wherein the agent is a maytansinoid.

65. The method according to claim 16, wherein the subject is human.

66. The method according to claim 16, wherein the tumor cell is selected from the group consisting of breast, testicular, colon, lung, ovary, bladder, uterine, cervical, pancreatic, and stomach tumor cells.

67. The method of claim 16, wherein the antibody is a humanized antibody.

68. The method of claim 16, wherein the antibody is a human antibody.

69. The method of claim 16, wherein the antibody is an antibody fragment selected from the group consisting of a Fab, a Fab', and a F(ab')2 fragment.

70. The method of claim 16, wherein the antibody is a full length antibody.

71. The method of claim 16, wherein the antibody is a single chain antibody.

72. The method according to claim 17, wherein the subject is human.

73. The method according to claim 17, wherein the tumor cell is selected from the group consisting of breast, testicular, colon, lung, ovary, bladder, uterine, cervical, pancreatic, and stomach tumor cells.

74. The method of claim 17, wherein the antibody is an antibody fragment selected from the group consisting of a Fab, a Fab', and a F(ab')2 fragment.

75. The method of claim 17, wherein the antibody is a full length antibody.

76. The method of claim 17, wherein the antibody is a single chain antibody.

77. The method of claim 17, wherein the antibody is administered in combination with a chemotherapeutic agent which is not conjugated to the antibody.

78. The method of claim 17, wherein the antibody is conjugated to a chemotherapeutic agent.

79. The method of claim 78, wherein the chemotherapeutic agent is selected from the group consisting of a tumor-activated prodrug, a radionuclide and a toxin.

80. The antibody of claim 79, wherein the agent is a maytansinoid.

81. The method according to claim 18, wherein the subject is human.

82. The method according to claim 18, wherein the tumor cell is selected from the group consisting of breast, testicular, colon, lung, ovary, bladder, uterine, cervical, pancreatic, and stomach tumor cells.

83. The method of claim 18, wherein the antibody is a humanized antibody.

84. The method of claim 18, wherein the antibody is a human antibody.

85. The method of claim 18, wherein the antibody is an antibody fragment selected from the group consisting of a Fab, a Fab', and a F(ab')2 fragment.

86. The method of claim 18, wherein the antibody is a full length antibody.

87. The method of claim 18, wherein the antibody is a single chain antibody.

88. The method of claim 18, wherein the antibody is administered in combination with a chemotherapeutic agent which is not conjugated to the antibody.

89. The method of claim 18, wherein the antibody is conjugated to a chemotherapeutic agent.

90. The method of claim 89, wherein the chemotherapeutic agent is selected from the group consisting of a tumor-activated prodrug, a radionuclide and a toxin.

91. The antibody of claim 90, wherein the agent is a maytansinoid.

92. The method according to claim 19, wherein the subject is human.

93. The method according to claim 19, wherein the tumor cell is selected from the group consisting of breast, testicular, colon, lung, ovary, bladder, uterine, cervical, pancreatic, and stomach tumor cells.

94. The method of claim 19, wherein the antibody is a humanized antibody.

95. The method of claim 19, wherein the antibody is a human antibody.

96. The method of claim 19, wherein the antibody is an antibody fragment selected from the group consisting of a Fab, a Fab', and a F(ab')2 fragment.

97. The method of claim 19, wherein the antibody is a full length antibody.

98. The method of claim 19, wherein the antibody is a single chain antibody.

99. The method of claim 19, wherein the antibody is administered in combination with a chemotherapeutic agent which is not conjugated to the antibody.

100. The method of claim 19, wherein the antibody is conjugated to a chemotherapeutic agent.

101. The method of claim 100, wherein the chemotherapeutic agent is selected from the group consisting of a tumor-activated prodrug, a radionuclide and a toxin.

102. The antibody of claim 101, wherein the agent is a maytansinoid.

103. The method according to claim 20, wherein the subject is human.

104. The method according to claim 20, wherein the tumor cell is selected from the group consisting of breast, testicular, colon, lung, ovary, bladder, uterine, cervical, pancreatic, and stomach tumor cells.

105. The method of claim 20, wherein the antibody is a humanized antibody.

106. The method of claim 20, wherein the antibody is a human antibody.

107. The method of claim 20, wherein the antibody is an antibody fragment selected from the group consisting of a Fab, a Fab', and a F(ab')2 fragment.

108. The method of claim 20, wherein the antibody is a full length antibody.

109. The method of claim 20, wherein the antibody is a single chain antibody.

110. The method of claim 20, wherein the antibody is administered in combination with a chemotherapeutic agent which is not conjugated to the antibody.

111. The method of claim 20, wherein the antibody is conjugated to a chemotherapeutic agent.

112. The method of claim 111, wherein the chemotherapeutic agent is selected from the group consisting of a tumor-activated prodrug, a radionuclide and a toxin.

113. The antibody of claim 112, wherein the agent is a maytansinoid.

114. The method according to claim 21, wherein the subject is human.

115. The method according to claim 21, wherein the tumor cell is selected from the group consisting of breast, testicular, colon, lung, ovary, bladder, uterine, cervical, pancreatic, and stomach tumor cells.

116. The method of claim 21, wherein the antibody is a humanized antibody.

117. The method of claim 21, wherein the antibody is a human antibody.

118. The method of claim 21, wherein the antibody is an antibody fragment selected from the group consisting of a Fab, a Fab', and a F(ab')2 fragment.

119. The method of claim 21, wherein the antibody is a full length antibody.

120. The method of claim 21, wherein the antibody is a single chain antibody.

121. The method of claim 21, wherein the antibody is administered in combination with a chemotherapeutic agent which is not conjugated to the antibody.

122. The method of claim 21, wherein the antibody is conjugated to a chemotherapeutic agent.

123. The method of claim 122, wherein the chemotherapeutic agent is selected from the group consisting of a tumor-activated prodrug, a radionuclide and a toxin.

124. The antibody of claim 123, wherein the agent is a maytansinoid.

125. The method according to claim 22, wherein the subject is human.

126. The method according to claim 22, wherein the tumor cell is selected from the group consisting of breast, testicular, colon, lung, ovary, bladder, uterine, cervical, pancreatic, and stomach tumor cells.

127. The method of claim 22, wherein the antibody is a humanized antibody.

128. The method of claim 22, wherein the antibody is a human antibody.

129. The method of claim 22, wherein the antibody is an antibody fragment selected from the group consisting of a Fab, a Fab', and a F(ab')2 fragment.

130. The method of claim 22, wherein the antibody is a full length antibody.

131. The method of claim 22, wherein the antibody is a single chain antibody.

132. The method of claim 22, wherein the antibody is administered in combination with a chemotherapeutic agent which is not conjugated to the antibody.

133. The method of claim 22, wherein the antibody is conjugated to a chemotherapeutic agent.

134. The method of claim 133, wherein the chemotherapeutic agent is selected from the group consisting of a tumor-activated prodrug, a radionuclide and a toxin.

135. The antibody of claim 134, wherein the agent is a maytansinoid.

136. The method according to claim 23, wherein the subject is human.

137. The method according to claim 23, wherein the tumor cell is selected from the group consisting of breast, testicular, colon, lung, ovary, bladder, uterine, cervical, pancreatic, and stomach tumor cells.

138. The method of claim 23, wherein the antibody is a humanized antibody.

139. The method of claim 23, wherein the antibody is a human antibody.

140. The method of claim 23, wherein the antibody is an antibody fragment selected from the group consisting of a Fab, a Fab', and a F(ab')2 fragment.

141. The method of claim 23, wherein the antibody is a full length antibody.

142. The method of claim 23, wherein the antibody is a single chain antibody.

143. The method of claim 23, wherein the antibody is administered in combination with a chemotherapeutic agent which is not conjugated to the antibody.

144. The method of claim 23, wherein the antibody is conjugated to a chemotherapeutic agent.

145. The method of claim 144, wherein the chemotherapeutic agent is selected from the group consisting of a tumor-activated prodrug, a radionuclide and a toxin.

146. The antibody of claim 145, wherein the agent is a maytansinoid.

147. The method according to claim 24, wherein the subject is human.

148. The method according to claim 24, wherein the tumor cell is selected from the group consisting of breast, testicular, colon, lung, ovary, bladder, uterine, cervical, pancreatic, and stomach tumor cells.

149. The method of claim 24, wherein the antibody is a humanized antibody.

150. The method of claim 24, wherein the antibody is a human antibody.

151. The method of claim 24, wherein the antibody is an antibody fragment selected from the group consisting of a Fab, a Fab', and a F(ab')2 fragment.

152. The method of claim 24, wherein the antibody is a full length antibody.

153. The method of claim 24, wherein the antibody is a single chain antibody.

154. The method of claim 24, wherein the antibody is administered in combination with a chemotherapeutic agent which is not conjugated to the antibody.

155. The method of claim 24, wherein the antibody is conjugated to a chemotherapeutic agent.

156. The method of claim 155, wherein the chemotherapeutic agent is selected from the group consisting of a tumor-activated prodrug, a radionuclide and a toxin.

157. The antibody of claim 156, wherein the agent is a maytansinoid.

158. The method according to claim 25, wherein the subject is human.

159. The method according to claim 25, wherein the tumor is selected from the group consisting of breast, testicular, colon, lung, ovary, bladder, uterine, cervical, pancreatic, and stomach tumors.

160. The method of claim 25, wherein the antibody is a humanized antibody.

161. The method of claim 25, wherein the antibody is a human antibody.

162. The method of claim 25, wherein the antibody is an antibody fragment selected from the group consisting of a Fab, a Fab', and a F(ab')2 fragment.

163. The method of claim 25, wherein the antibody is a full length antibody.

164. The method of claim 25, wherein the antibody is a single chain antibody.

165. The method according to claim 26, wherein the subject is human.

166. The method according to claim 26, wherein the tumor is selected from the group consisting of breast, testicular, colon, lung, ovary, bladder, uterine, cervical, pancreatic, and stomach tumors.

167. The method of claim 26, wherein the antibody is an antibody fragment selected from the group consisting of a Fab, a Fab', and a F(ab')2 fragment.

168. The method of claim 26, wherein the antibody is a full length antibody.

169. The method of claim 26, wherein the antibody is a single chain antibody.

170. The method of claim 26, wherein the antibody is administered in combination with a chemotherapeutic agent which is not conjugated to the antibody.

171. The method of claim 26, wherein the antibody is conjugated to a chemotherapeutic agent.

172. The method of claim 171, wherein the chemotherapeutic agent is selected from the group consisting of a tumor-activated prodrug, a radionuclide and a toxin.

173. The antibody of claim 172, wherein the agent is a maytansinoid.

174. The method according to claim 27, wherein the subject is human.

175. The method according to claim 27, wherein the tumor is selected from the group consisting of breast, testicular, colon, lung, ovary, bladder, uterine, cervical, pancreatic, and stomach tumors.

176. The method of claim 27, wherein the antibody is a humanized antibody.

177. The method of claim 27, wherein the antibody is a human antibody.

178. The method of claim 27, wherein the antibody is an antibody fragment selected from the group consisting of a Fab, a Fab', and a F(ab')2 fragment.

179. The method of claim 27, wherein the antibody is a full length antibody.

180. The method of claim 27, wherein the antibody is a single chain antibody.

181. The method of claim 27, wherein the antibody is administered in combination with a chemotherapeutic agent which is not conjugated to the antibody.

182. The method of claim 27, wherein the antibody is conjugated to a chemotherapeutic agent.

183. The method of claim 182, wherein the chemotherapeutic agent is selected from the group consisting of a tumor-activated prodrug, a radionuclide and a toxin.

184. The antibody of claim 183, wherein the agent is a maytansinoid.

185. The method according to claim 28, wherein the subject is human.

186. The method according to claim 28, wherein the tumor is selected from the group consisting of breast, testicular, colon, lung, ovary, bladder, uterine, cervical, pancreatic, and stomach tumors.

187. The method of claim 28, wherein the antibody is a humanized antibody.

188. The method of claim 28, wherein the antibody is a human antibody.

189. The method of claim 28, wherein the antibody is an antibody fragment selected from the group consisting of a Fab, a Fab', and a F(ab')2 fragment.

190. The method of claim 28, wherein the antibody is a full length antibody.

191. The method of claim 28, wherein the antibody is a single chain antibody.

192. The method of claim 28, wherein the antibody is administered in combination with a chemotherapeutic agent which is not conjugated to the antibody.

193. The method of claim 28, wherein the antibody is conjugated to a chemotherapeutic agent.

194. The method of claim 193, wherein the chemotherapeutic agent is selected from the group consisting of a tumor-activated prodrug, a radionuclide and a toxin.

195. The antibody of claim 194, wherein the agent is a maytansinoid.

196. The method according to claim 29, wherein the subject is human.

197. The method according to claim 29, wherein the tumor is selected from the group consisting of breast, testicular, colon, lung, ovary, bladder, uterine, cervical, pancreatic, and stomach tumors.

198. The method of claim 29, wherein the antibody is a humanized antibody.

199. The method of claim 29, wherein the antibody is a human antibody.

200. The method of claim 29, wherein the antibody is an antibody fragment selected from the group consisting of a Fab, a Fab', and a F(ab')2 fragment.

201. The method of claim 29, wherein the antibody is a full length antibody.

202. The method of claim 29, wherein the antibody is a single chain antibody.

203. The method of claim 29, wherein the antibody is administered in combination with a chemotherapeutic agent which is not conjugated to the antibody.

204. The method of claim 29, wherein the antibody is conjugated to a chemotherapeutic agent.

205. The method of claim 204, wherein the chemotherapeutic agent is selected from the group consisting of a tumor-activated prodrug, a radionuclide and a toxin.

206. The antibody of claim 205, wherein the agent is a maytansinoid.

207. The method according to claim 30, wherein the subject is human.

208. The method according to claim 30, wherein the tumor is selected from the group consisting of breast, testicular, colon, lung, ovary, bladder, uterine, cervical, pancreatic, and stomach tumors.

209. The method of claim 30, wherein the antibody is a humanized antibody.

210. The method of claim 30, wherein the antibody is a human antibody.

211. The method of claim 30, wherein the antibody is an antibody fragment selected from the group consisting of a Fab, a Fab', and a F(ab')2 fragment.

212. The method of claim 30, wherein the antibody is a full length antibody.

213. The method of claim 30, wherein the antibody is a single chain antibody.

214. The method of claim 30, wherein the antibody is administered in combination with a chemotherapeutic agent which is not conjugated to the antibody.

215. The method of claim 30, wherein the antibody is conjugated to a chemotherapeutic agent.

216. The method of claim 215, wherein the chemotherapeutic agent is selected from the group consisting of a tumor-activated prodrug, a radionuclide and a toxin.

217. The antibody of claim 216, wherein the agent is a maytansinoid.

218. The method according to claim 31, wherein the subject is human.

219. The method according to claim 31, wherein the tumor is selected from the group consisting of breast, testicular, colon, lung, ovary, bladder, uterine, cervical, pancreatic, and stomach tumors.

220. The method of claim 31, wherein the antibody is a humanized antibody.

221. The method of claim 31, wherein the antibody is a human antibody.

222. The method of claim 31, wherein the antibody is an antibody fragment selected from the group consisting of a Fab, a Fab', and a F(ab')2 fragment.

223. The method of claim 31, wherein the antibody is a full length antibody.

224. The method of claim 31, wherein the antibody is a single chain antibody.

225. The method of claim 31, wherein the antibody is administered in combination with a chemotherapeutic agent which is not conjugated to the antibody.

226. The method of claim 31, wherein the antibody is conjugated to a chemotherapeutic agent.

227. The method of claim 226, wherein the chemotherapeutic agent is selected from the group consisting of a tumor-activated prodrug, a radionuclide and a toxin.

228. The antibody of claim 227, wherein the agent is a maytansinoid.

* * * * *

UNITED STATES PATENT AND TRADEMARK OFFICE
CERTIFICATE OF CORRECTION

| | | |
|---|---|---|
| PATENT NO. | : 7,531,174 B2 | Page 1 of 1 |
| APPLICATION NO. | : 10/693538 | |
| DATED | : May 12, 2009 | |
| INVENTOR(S) | : Sanicola-Nadel et al. | |

It is certified that error appears in the above-identified patent and that said Letters Patent is hereby corrected as shown below:

On the Title page, Item (*) Notice should read --Subject to any disclaimer, the term of this patent is extended or adjusted under 35 USC 154(b) by 210 days.--

Signed and Sealed this

Twenty-fifth Day of August, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,531,174 B2 | Page 1 of 1 |
| APPLICATION NO. | : 10/693538 | |
| DATED | : May 12, 2009 | |
| INVENTOR(S) | : Sanicola-Nadel et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (233) days Delete the phrase "by 233 days" and insert -- by 210 days --

Signed and Sealed this

Twentieth Day of October, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,531,174 B2 | Page 1 of 1 |
| APPLICATION NO. | : 10/693538 | |
| DATED | : May 12, 2009 | |
| INVENTOR(S) | : Sanicola-Nadel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 531 days.

Signed and Sealed this
Seventeenth Day of July, 2012

David J. Kappos
*Director of the United States Patent and Trademark Office*